(12) United States Patent
Carlsson et al.

(10) Patent No.: US 9,540,625 B2
(45) Date of Patent: Jan. 10, 2017

(54) HUMAN CARBONIC ANHYDRASE II WITH INCREASED PHYSICAL STABILITY

(71) Applicant: Inzymes Biotech AB, Linkoping (SE)

(72) Inventors: Uno Carlsson, Söderköping (SE); Martin Karlsson, Linköping (SE)

(73) Assignee: Inzymes Biotech AB, Linkoping (SE)

( * ) Notice: Subject to any disclaimer, the term of this patent is extended or adjusted under 35 U.S.C. 154(b) by 0 days.

(21) Appl. No.: 14/382,462

(22) PCT Filed: Apr. 11, 2013

(86) PCT No.: PCT/SE2013/050392
§ 371 (c)(1),
(2) Date: Sep. 2, 2014

(87) PCT Pub. No.: WO2013/162445
PCT Pub. Date: Oct. 31, 2013

(65) Prior Publication Data
US 2015/0191711 A1    Jul. 9, 2015

(30) Foreign Application Priority Data

Apr. 23, 2012  (SE) ...................................... 1250400

(51) Int. Cl.
*C12N 9/88*       (2006.01)
*C07H 21/04*      (2006.01)
*B01D 53/84*      (2006.01)

(52) U.S. Cl.
CPC ................. *C12N 9/88* (2013.01); *B01D 53/84* (2013.01); *C12Y 402/01001* (2013.01); *B01D 2255/804* (2013.01); *B01D 2257/504* (2013.01); *Y02C 10/02* (2013.01)

(58) Field of Classification Search
None
See application file for complete search history.

(56) References Cited

U.S. PATENT DOCUMENTS

| 8,354,261 B2 | 1/2013 | Alvizo et al. |
| 2012/0009653 A1 | 1/2012 | Alvizo |

FOREIGN PATENT DOCUMENTS

| WO | 2012/003277 A2 | 1/2012 |

OTHER PUBLICATIONS

UniProt Q50940, CAH Neigo, Created Jul. 15, 1999.*
International Search Report for PCT/SE2013/050392, ISA/SE, Stockholm, mailed Jul. 1, 2013.
Written Opinion dated Jun. 25, 2013 from the priority international application.
Martin Karlsson; Denaturate-Assisted Formation of a Stabilizing Disulfide Bridge from Engineered Cysteines in Nonideal Conformations; Biochemistry 2005/ V.44; p. 3487-3493.
Response to Written Opinion dated Feb. 14, 2014 from the priority international application.
D. Shortie; The Denatured State (the other half of the folding equation) and its Role in Protein Stability; FASEB Journal; p. 27-34, v 10, Jan. 1996.

\* cited by examiner

*Primary Examiner* — Iqbal H Chowdhury
(74) *Attorney, Agent, or Firm* — Harness, Dickey & Pierce, P.L.C.

(57) ABSTRACT

An isolated polypeptide having carbonic anhydrase activity, the sequence of which corresponds to modified human carbonic anhydrase II is described. The isolated polypeptide comprises the mutations A23C, S99C, L202C, C205S and V241C and the polypeptide has increased physical stability compared to wild type carbonic anhydrase II. Further, the polypeptide comprises disulfide bridges between C23 and C202 and/or between C99 and C241.

10 Claims, 7 Drawing Sheets

SEQUENCE LISTING

```
<160> NUMBER OF SEQ ID NOS: 9

<210> SEQ ID NO 1
<211> LENGTH: 783
<212> TYPE: DNA
<213> ORGANISM: Artificial Sequence
<220> FEATURE:
<223> OTHER INFORMATION: Modified human carbonic anhydrase II

<400> SEQUENCE: 1
atggcccatc actgggggta cggcaaacac aacggacctg agcactggca taaggacttc       60
cccattgcca agggagagcg ccagtcccct gttgacatcg acactcatac agccaagtat      120
gacccttccc tgaagcccct gtctgtttcc tatgatcaag caacttccct gaggatcctc      180
aacaatggtc atgctttcaa cgtggagttt gatgactctc aggacaaagc agtgctcaag      240
ggaggacccc tggatggcac ttacagattg attcagtttc actttcactg gggttcactt      300
gatggacaag gttcagagca tactgtggat aaaaagaaat atgctgcaga acttcacttg      360
gttcactgga acaccaaata tggggatttt gggaaagctg tgcagcaacc tgatggactg      420
gccgttctag gtattttttt gaaggttggc agcgctaaac cgggccttca gaaagttgtt      480
gatgtgctgg attccattaa aacaaagggc aagagtgctg acttcactaa cttcgatcct      540
cgtggcctcc ttcctgaatc cctggattac tggacctacc caggctcact gaccacccct      600
cctcttctgg aatctgtgac ctggattgtg ctcaaggaac ccatcagcgt cagcagcgag      660
caggtgttga aattccgtaa acttaacttc aatggggagg gtgaacccga agaactgatg      720
gtggacaact ggcgcccagc tcagccactg aagaacaggc aaatcaaagc ttccttcaaa      780
taa                                                                    783

<210> SEQ ID NO 2
<211> LENGTH: 260
<212> TYPE: PRT
<213> ORGANISM: Artificial Sequence
<220> FEATURE:
<223> OTHER INFORMATION: Modified human carbonic anhydrase II

<400> SEQUENCE: 2

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
```

```
                85                  90                  95
Trp Gly Ser Leu Asp Gly Gln Gly Ser Glu His Thr Val Asp Lys Lys
            100                 105                 110
Lys Tyr Ala Ala Glu Leu His Leu Val His Trp Asn Thr Lys Tyr Gly
            115                 120                 125
Asp Phe Gly Lys Ala Val Gln Gln Pro Asp Gly Leu Ala Val Leu Gly
            130                 135                 140
Ile Phe Leu Lys Val Gly Ser Ala Lys Pro Gly Leu Gln Lys Val Val
145                 150                 155                 160
Asp Val Leu Asp Ser Ile Lys Thr Lys Gly Lys Ser Ala Asp Phe Thr
                165                 170                 175
Asn Phe Asp Pro Arg Gly Leu Leu Pro Glu Ser Leu Asp Tyr Trp Thr
            180                 185                 190
Tyr Pro Gly Ser Leu Thr Thr Pro Pro Leu Leu Glu Ser Val Thr Trp
            195                 200                 205
Ile Val Leu Lys Glu Pro Ile Ser Val Ser Ser Glu Gln Val Leu Lys
            210                 215                 220
Phe Arg Lys Leu Asn Phe Asn Gly Glu Gly Glu Pro Glu Glu Leu Met
225                 230                 235                 240
Val Asp Asn Trp Arg Pro Ala Gln Pro Leu Lys Asn Arg Gln Ile Lys
                245                 250                 255
Ala Ser Phe Lys
            260

<210> SEQ ID NO 3
<211> LENGTH: 783
<212> TYPE: DNA
<213> ORGANISM: Artificial Sequence
<220> FEATURE:
<223> OTHER INFORMATION: Modified human carbonic anhydrase II

<400> SEQUENCE: 3
atggcccatc actgggggta cggcaaacac aacggacctg agcactggca taaggacttc    60
cccattgcca agggagagcg ccagtcccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagtttc actttcactg gggttgcctt   300
gatggacaag gttcagagca tactgtggat aaaaagaaat atgctgcaga acttcacttg   360
gttcactgga caccaaata tggggatttt gggaaagctg tgcagcaacc tgatggactg   420
gccgttctag gtatttttt gaaggttggc agcgctaaac cgggccttca gaaagttgtt   480
gatgtgctgg attccattaa acaaagggc aagagtgctg acttcactaa cttcgatcct   540
cgtggcctcc ttcctgaatc cctggattac tggacctacc caggctcact gaccaccct   600 cctcttctgg aatctgtgac ctggattgtg ctcaaggaac ccatcagcgt cagcagcgag   660
caggtgttga aattccgtaa acttaacttc aatggggagg gtgaacccga gaactgatg   720 tgcgacaact ggcgcccagc tcagccactg aagaacaggc aaatcaaagc ttccttcaaa   780
taa                                                                 783

<210> SEQ ID NO 4
<211> LENGTH: 260
<212> TYPE: PRT
<213> ORGANISM: Artificial Sequence
<220> FEATURE:
```

```
<223> OTHER INFORMATION: Modified human carbonic anhydrase II
<220> FEATURE:
<221> NAME/KEY: BINDING
<222> LOCATION: (99)..(241)
<223> OTHER INFORMATION: Disulfide bridge between aa in position 99 and
      aa in position 241

<400> SEQUENCE: 4
```

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65              70                  75                  80

Gly Gly Pro Leu Asp Gly Thr Tyr Arg Leu Ile Gln Phe His Phe His
                85                  90                  95

Trp Gly Cys Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Ser Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240

Cys Asp Asn Trp Arg Pro Ala Gln Pro Leu Lys Asn Arg Gln Ile Lys
                245                 250                 255

Ala Ser Phe Lys
        260

```
<210> SEQ ID NO 5
<211> LENGTH: 783
<212> TYPE: DNA
<213> ORGANISM: Artificial Sequence
<220> FEATURE:
<223> OTHER INFORMATION: Modified human carbonic anhydrase II

<400> SEQUENCE: 5
```

| | | | | | |
|---|---|---|---|---|---|
| atggcccatc | actgggggta | cggcaaacac | aacggacctg | agcactggca | taaggacttc | 60
| cccatttgca | agggagagcg | ccagtcccct | gttgacatcg | acactcatac | agccaagtat | 120
| gaccccttcc | ctgaagcccct | gtctgttttcc | tatgatcaag | caacttccct | gaggatcctc | 180
| aacaatggtc | atgctttcaa | cgtggagttt | gatgactctc | aggacaaagc | agtgctcaag | 240
| ggaggacccc | tggatggcac | ttacagattg | attcagtttc | actttcactg | gggttcactt | 300

```
gatggacaag gttcagagca tactgtggat aaaaagaaat atgctgcaga acttcacttg    360
gttcactgga acaccaaata tggggatttt gggaaagctg tgcagcaacc tgatggactg    420
gccgttctag gtattttttt gaaggttggc agcgctaaac cgggccttca gaaagttgtt    480
gatgtgctgg attccattaa acaaagggc aagagtgctg acttcactaa cttcgatcct     540
cgtggcctcc ttcctgaatc cctggattac tggacctacc caggctcact gaccaccctt    600
ccttgtctgg aatctgtgac ctggattgtg ctcaaggaac ccatcagcgt cagcagcgag    660
caggtgttga aattccgtaa acttaacttc aatggggagg gtgaacccga agaactgatg    720
gtggacaact ggcgcccagc tcagccactg aagaacaggc aaatcaaagc ttccttcaaa    780
taa                                                                  783
```

<210> SEQ ID NO 6
<211> LENGTH: 260
<212> TYPE: PRT
<213> ORGANISM: Artificial Sequence
<220> FEATURE:
<223> OTHER INFORMATION: Modified human carbonic anhydrase II
<220> FEATURE:
<221> NAME/KEY: BINDING
<222> LOCATION: (23)..(202)
<223> OTHER INFORMATION: Disulfide bridge between aa in position 23 and
      aa in position 202

<400> SEQUENCE: 6

```
Met Ser His His Trp Gly Tyr Gly Lys His Asn Gly Pro Glu His Trp
1               5                   10                  15

His Lys Asp Phe Pro Ile Cys Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Cys Leu Glu Ser Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240
```

Val Asp Asn Trp Arg Pro Ala Gln Pro Leu Lys Asn Arg Gln Ile Lys
            245                 250                 255

Ala Ser Phe Lys
            260

<210> SEQ ID NO 7
<211> LENGTH: 783
<212> TYPE: DNA
<213> ORGANISM: Artificial Sequence
<220> FEATURE:
<223> OTHER INFORMATION: Modified human carbonic anhydrase II

<400> SEQUENCE: 7

```
atggcccatc actgggggta cggcaaacac aacggacctg agcactggca taaggacttc      60
cccatttgca agggagagcg ccagtcccct gttgacatcg acactcatac agccaagtat     120
gacccttccc tgaagcccct gtctgtttcc tatgatcaag caacttccct gaggatcctc     180
aacaatggtc atgctttcaa cgtggagttt gatgactctc aggacaaagc agtgctcaag     240
ggaggacccc tggatggcac ttacagattg attcagtttc actttcactg gggttgcctt     300
gatggacaag gttcagagca tactgtggat aaaagaaat atgctgcaga acttcacttg     360
gttcactgga acaccaaata tggggattt gggaaagctg tgcagcaacc tgatggactg     420
gccgttctag gtatttttt gaaggttggc agcgctaaac cgggccttca gaaagttgtt     480
gatgtgctgg attccattaa acaaaagggc aagagtgctg acttcactaa cttcgatcct     540
cgtggcctcc ttcctgaatc cctggattac tggacctacc caggctcact gaccaccct     600
ccttgtctgg aatctgtgac ctggattgtg ctcaaggaac ccatcagcgt cagcagcgag     660
caggtgttga aattccgtaa acttaacttc aatggggagg gtgaaccga agaactgatg     720
tgcgacaact ggcgcccagc tcagccactg aagaacaggc aaatcaaagc ttccttcaaa     780
taa                                                                   783
```

<210> SEQ ID NO 8
<211> LENGTH: 260
<212> TYPE: PRT
<213> ORGANISM: Artificial Sequence
<220> FEATURE:
<223> OTHER INFORMATION: Modified human carbonic anhydrase II
<220> FEATURE:
<221> NAME/KEY: BINDING
<222> LOCATION: (23)..(202)
<223> OTHER INFORMATION: Disulfide bridge between aa in position 23 and
      aa in position 202
<220> FEATURE:
<221> NAME/KEY: BINDING
<222> LOCATION: (99)..(241)
<223> OTHER INFORMATION: Disulfide bridge between aa in position 99 and
      aa in position 241

<400> SEQUENCE: 8

Met Ser His His Trp Gly Tyr Gly Lys His Asn Gly Pro Glu His Trp
1               5                   10                  15

His Lys Asp Phe Pro Ile Cys Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

```
Gly Gly Pro Leu Asp Gly Thr Tyr Arg Leu Ile Gln Phe His Phe His
                85                  90                  95

Trp Gly Cys Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Cys Leu Glu Ser Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240

Cys Asp Asn Trp Arg Pro Ala Gln Pro Leu Lys Asn Arg Gln Ile Lys
                245                 250                 255

Ala Ser Phe Lys
            260

<210> SEQ ID NO 9
<211> LENGTH: 260
<212> TYPE: PRT
<213> ORGANISM: Homo sapiens

<400> SEQUENCE: 9

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190
```

```
Tyr Pro Gly Ser Leu Thr Thr Pro Pro Leu Leu Glu Cys Val Thr Trp
        195             200             205

Ile Val Leu Lys Glu Pro Ile Ser Val Ser Ser Glu Gln Val Leu Lys
    210             215             220

Phe Arg Lys Leu Asn Phe Asn Gly Glu Gly Glu Pro Glu Glu Leu Met
225             230             235             240

Val Asp Asn Trp Arg Pro Ala Gln Pro Leu Lys Asn Arg Gln Ile Lys
            245             250             255

Ala Ser Phe Lys
            260
```

HUMAN CARBONIC ANHYDRASE II WITH INCREASED PHYSICAL STABILITY

CROSS-REFERENCE TO RELATED APPLICATIONS

This application is a 371 U.S. National Stage of International Application No. PCT/SE2013/050392, filed Apr. 11, 2013. This application claims the benefit of Swedish Patent Application No. 1250400-7, filed Apr. 23, 2012. The entire disclosures of the above applications are incorporated herein by reference.

TECHNICAL FIELD OF THE INVENTION

The present invention relates to an engineered variant of the enzyme human carbonic anhydrase II with increased physical stability as defined by increased thermodynamic, thermal and kinetic stability as compared to the wild type enzyme. The present invention also relates to a method of increasing the physical stability of carbonic anhydrases. Furthermore, the invention relates to the use of said enzyme in any technical application used for $CO_2$ extraction from a medium. Furthermore, the present invention also relates to isolated polynucleotides encoding the polypeptide as well as isolated polypeptides. The invention also relates to nucleic acid constructs and vectors comprising the polynucleotides.

BACKGROUND ART

Carbonic anhydrases (CA, EC 4.2.2.1) is a group of enzymes that catalyzes the reversible reaction of carbon dioxide and water into bicarbonate and proton according to:

Carbonic anhydrases are widely distributed throughout nature and are categorized in five distinct classes, the α-, β-, γ-, δ-, and ξ-class[1]. The α-class carbonic anhydrases can be found in vertebrates, bacteria, algae and green plants whereas β-class carbonic anhydrases are found in bacteria, algae and chloroplasts. One of each δ and ξ-class carbonic anhydrases have been isolated from eukaryotic marine diatoms. The only γ-class carbonic anhydrase (Cam) isolated so far has been isolated from the thermophilic Archaeon *Methanosarcina thermophila*[2]. However, since the five classes have evolved through convergent evolution they differ significantly from each other with regard to amino acid sequence, structure and activity. The α-class carbonic anhydrases belongs to a superfamily of homologous proteins i.e. their genes have evolved from a common ancestral gene. Among the most effective carbonic anhydrases are the α-carbonic anhydrases from vertebrates with a turn over number ($k_{cat}$) of up to $1.4 \cdot 10^6$ s$^{-1}$, which is $10^7$ times faster than the spontaneous reaction. Furthermore, the catalytic efficiency ($k_{cat}/K_m$) for e.g. human carbonic anhydrase II is $1.5 \cdot 10^8$ M$^{-1}$ s$^{-1}$, which is close to a diffusion controlled reaction. Since the natural function of the enzyme is e.g. to facilitate the removal of $CO_2$ from the blood (human carbonic anhydrase II) it has been suggested that carbonic anhydrases can be used as biological catalysts in bioreactors designed for capturing $CO_2$ from various gas streams. At this time there is a consensus view that the concentration of carbon dioxide in the atmosphere is the major contributor to increasing global warming, which has also been concluded by the Intergovernmental Panel on Climate Change (IPCC)[3]. Thus, several chemical methods have been suggested and tested for carbon capture and sequestration (CCS). However, most of these operate at extreme pressure or temperature and use harmful chemical compounds and still consume high amounts of energy at low efficiency. If, instead, an enzyme based bioreactor utilizing carbonic anhydrase as a catalyst could be used, this could solve the energy and environmental problem with chemical reactors. Several such bioreactors and processes have been suggested in e.g. WO2006/089423, U.S. Pat. No. 6,524, 842, WO2004/007058, WO 2004/028667, U.S. 2004/0029257, U.S. Pat. No. 7,132, 090, WO 2005/114417, U.S. Pat. No. 6,143,556, WO 2004/104160, US 2005/214936 and U.S. Pat. No. 7,892,814. The aforementioned processes generally operate by bringing carbonic anhydrase, either free in solution or immobilized, in contact with $CO_2$ dissolved in the solution. However, since the operational conditions such as temperature, pH and chemical composition of the solution etc can vary widely depending on application, neither of these processes is of any value if the necessary carbonic anhydrase catalyst is not stable enough to function at the operational conditions or have long enough life time to be economically viable.

Unfortunately, since there are no organisms living under the conditions that can prevail in a $CO_2$-capturing bioreactor, nature has not provided us with a carbonic anhydrase with the desired stability or efficiency. Mammalian, plant and prokaryotic carbonic anhydrases have through natural evolution been selected to be stable at the physiological condition of the respective organism. Thus, α- and β class carbonic anhydrases are generally only stable at physiological conditions, i.e. approximately 37° C. or lower. The only heat-stable carbonic anhydrase has been found in *Methanosarcina thermophila*, which has an optimal growth at 55° C. and produces a γ-carbonic anhydrase (Cam) with a heat denaturation temperature (melting point, $T_m$) of about 70° C. However, this enzyme has a catalytic turn over that is approximately a 10-fold slower than that of e.g. human carbonic anhydrase II ($k_{cat}$ of approx. $1.2 \cdot 10^5$ s$^{-1}$ as compared to $1.4 \cdot 10^6$ s$^{-1}$). Furthermore, the catalytic efficiency is approximately 20-fold lower ($7.5 \cdot 10^6$ M$^{-1} \cdot $s$^{-1}$) as compared to the $1.5 \cdot 10^8$ M$^{-1} \cdot $s$^{-1}$ for human carbonic anhydrase II[4, 5]. Other features of γ-carbonic anhydrase from *Methanosarcina thermophila* that makes it less interesting as a catalyst for a bioreactor is that it is a homotrimeric protein, i.e. an enzyme built up from three identical polypeptide chains. Each of the polypeptides contains 213 amino acids and has a molecular weight of approx. 23 kD, i.e. a total of 639 amino acids and a molecular weight of 69.15 kD. This can be compared to HCA II which is a monomeric protein of 259 amino acids and a molecular weight of 29.3 kD[6]. Thus, an advantage of HCA II, as compared to Cam, is that it will not be inactivated by dissociation of polypeptides. Another problem associated with the use of γ-carbonic anhydrase from *Methanosarcina thermophila* is that to obtain the most active form of the enzyme (Fe$^{2+}$-Cam) it needs to be produced anaerobically and to be protected from air during purification and use. If these prerequisites are not met, the naturally occurring Fe$^{2+}$ in the active site is oxidized to Fe$^{3+}$ and subsequently exchanged by Zn$^{2+}$, which lowers the activity an additional 3-fold[6,7].

The conversion rate and efficiency is of course of great importance for the technical and economical feasibility of using carbonic anhydrases in any $CO_2$-capturing process. Thus, if it would be possible to use human carbonic anhydrase II, a bioreactor would require 10-20 times less enzyme (alternatively be 10-20 times smaller with the same amount of enzyme) than a corresponding reactor using e.g. γ-carbonic anhydrase from *Methanosarcina thermophila*.

Enzymes are macromolecular protein biomolecules that are able to function as highly effective, high-performing biological catalysts and are fundamental for all biological life. They are substances that accelerate the chemical reactions of life without being consumed themselves in the reaction. Isolated enzymes are important in many industrial processes for treating biological substrates. Thus, enzymes for industrial and environmental applications have a large and increasing economical and ecological value.

One bottleneck in the application of enzymes in industrial processes is that in order to be active, enzymes and other proteins must keep a highly ordered and folded structure. However, the highly ordered structure of proteins is only maintained if the proteins are stable at the prevailing conditions, i.e. pH, ionic strength, temperature, etc., within certain limits that are specific for each type of protein. In terms of natural selection of proteins during evolution, this notion stresses the fact that a protein molecule only makes structural sense when it exists under conditions similar to those for which it was selected, in its so called native state. Protein stability can fundamentally be divided in chemical stability and physical stability. Chemical stability relates to changes in activity of the enzyme in response to various chemical alterations, e.g. deamidation of aspargine to aspartate and oxidation of methionine. Changes in activity can be due to changes of the amino acids involved in the enzymatic process or due to that the chemically modified enzyme looses its structure and hence activity. Physical stability relates to the intrinsic ability of the protein to find and maintain its structure (and hence activity). Physical stability can be measured in several ways, e.g. as the thermodynamic stability, the thermal stability and the kinetic stability which are all a function of the sum of interactions within the protein and between the protein and its surroundings.

Therefore, in the quest to design more stable proteins, it is important to understand the differences and benefits, as well as the underlying mechanisms, of each type of stability to be able to attain proteins with the desired increased stability.

Thermodynamic stability is a measure of the difference in free energy ($\Delta G$) between the inactive unfolded (U) states and the folded state (F) in which the enzyme is active. Thermodynamic stability can be determined at equilibrium conditions if the protein is free to unfold and re-fold. This two-state model can be written as:

$$F \leftrightharpoons U$$

Thus, in this case the stability is simply the difference in free energy between the U and the F states ($\Delta G = G_{Unfolded} - G_{Folded}$) and the stability is defined as $\Delta G_{FU}$, where $$\Delta G_{FU} = -RT \ln K.$$

K represents the equilibrium constant between the unfolded and the folded state (K=[U]/[F]) and, therefore, the more thermodynamically stable the protein is the larger the difference in free energy ($\Delta G$) is. This can also be graphically represented by plotting the difference in free energy between the unfolded and native state. (See FIG. 1).

Thus, simplified, the thermodynamic stability can be increased by either destabilizing the unfolded state (higher free energy of U) or stabilizing the native state (lower free energy of F) so as to maximize the difference in free energy ($\Delta G_{FU}$) between the two states. The change in free energy needs to be lower than zero ($\Delta G<0$) for the folding reaction to be efficient, that is, favoring the native state of the protein. Since the difference in free energy is determined by its enthalpy ($\Delta H$, interactions) and entropy ($\Delta S$, disorder) according to $\Delta G = \Delta H - T\Delta S$ a favorable $\Delta G$ can be accomplished by strengthening the interactions of the folded state, leading to lowered enthalpy (e.g. hydrogen bonds, ion bonds, better packing of the protein interior etc.). The same, i.e. a larger difference in free energy between the unfolded and folded state, can be accomplished by destabilizing the unfolded state. Furthermore, for the unfolded state, which can be assumed to be a random coil, the same can be accomplished by restraining the freedom of the unfolded state leading to lowered entropy of the unfolded states and thereby a higher level of free energy for the unfolded state.

The melting point ($T_m$) of a protein, i.e. the midpoint temperature of unfolding, is a measure of a proteins thermal stability. In industrial processes it is often desirable to use enzymes with a high melting point since it is in many cases beneficial if the reaction can take place at an elevated temperature (higher rates of reaction, lower viscosity, less microbial growth, less fouling etc). For this reason, what is often focused on for proteins that have a potential use in industrial, enzyme based, processes is that the protein has a high thermal stability (i.e. a high melting point).

It is, however, important to recognize that at standard temperature (25° C.) the $\Delta G_{FU}$ values for a thermolabile protein are not necessarily lower than for a thermostable protein, i.e. a high thermal stability is not the same as a high thermodynamic stability at all temperatures[8]. Thus, it is not possible to deduce the melting point of a protein by simply determine its thermodynamic stability at ambient temperature or vice versa. The melting temperature ($T_m$) is the temperature at which U and F are at equilibrium and are equally populated and is determined by the $\Delta G_{FU}(T)$ function, and will occur when the denaturing pressure (temperature) is so high that $\Delta G_{FU}=0$. When $\Delta G_{FU}$ is plotted as a function of temperature, the $\Delta G_{FU}(T)$ function displays a skewed parabola that intersects the x-axis twice (i.e. both heat- and cold denaturation occurs) (see FIG. 2).

FIG. 2 illustrates how the thermostability of a hypothetic protein thus can be increased by other means than increasing the thermodynamic stability ($\Delta G_{UF}$) of the protein at standard temperatures.

Thus, thermal stability is related, but not equivalent, to thermodynamic stability. That is, at ambient temperatures a protein can have a relatively low thermodynamic stability and still prove to have a relatively high melting point.

Kinetic stability is a measure of at what rate a protein unfolds ($k_U$). This is especially important for proteins or conditions that denature proteins irreversibly to unfolded states. A protein can denature irreversibly if the protein in the unfolded state rapidly undergoes some permanent change such as proteolytic degradation or aggregation (which often is the case with thermally denatured proteins).

In these cases it is not the difference in free energy between the folded and unfolded state that is important. That will only affect the equilibrium and this is not a true equilibrium process. Instead, for kinetic stability, the important thing is the difference in free energy between the folded state (F) and the transition state (ts#) on the unfolding pathway which determines the activation energy for unfolding ($E_{A, unfolding}$). Hence, $E_{A, unfolding}$ determines the rate constant of unfolding ($k_U$) and thereby at what rate an irreversible inactivation of the unfolded state can take place (See FIG. 3).

Thus, this is in no way related to the thermodynamic stability ($\Delta G_{FU}$) or the thermal stability ($T_m$) and other means are necessary to increase the kinetic stability as compared to $\Delta G_{FU}$ and $T_m$. In order to change the free energy of the transition state the folding/unfolding mechanism of the protein needs to be affected. Simplified, when an ensemble of proteins fold they will mainly follow the fastest route that produces folding intermediates and transition states of lowest possible energy levels. However, if this route is no longer accessible, they will be forced to fold via an alternative route that has folding intermediates and transition states of higher energy. This will in effect lead to a route that places the transition state at a higher level of free energy. In this case, since the folded state has the same energy level as before (still needs to be in its highly ordered native fold to be active) the height of $E_{A,\ unfolding}$ will have increased and thus provide a barrier to unfolding leading to a slower unfolding rate constant ($k_U$).

Thus, for a protein to be valuable for any application it needs to have a large negative $\Delta G_{FU}$ at the temperature of operation so that the protein operates well below its melting point ($T_m$). Equally important is that it needs a high kinetic stability so that the protein is maintained in the natively folded state and the protein does not sample the unfolded state which will render it irreversibly inactive. Hence, a high kinetic stability will lead to slow unfolding and a long lifetime of the protein. This is true for all conditions and will for example increase shelf life of the protein at ambient temperatures, but the activation energy for unfolding ($E_{A,\ unfolding}$) will also provide a barrier for unfolding also if the protein operates close to or even above its unfolding point (thermal or other) and thus keeping the unfolding rate constant ($k_U$) low and the lifetime high also at conditions that induce unfolding.

There are numerous ways of stabilizing proteins[9], either by stabilizing the folded state or by destabilizing the unfolded state by different means. However, most methods to stabilize the folded state rely on strengthening local interactions that are only formed once the protein is folded and few will substantially affect the folding route and hence the kinetic stability. Furthermore, because of the often hundreds of amino acids to vary and the thousands of interactions within the protein and between the protein and the surroundings, it is very difficult to simply examine the structure and pinpoint what to change in order to increase the stability. This is also the reason why combinatory methods like directed evolution has been developed. Since these methods produce thousands of variants of the protein "by chance", which are subsequently tested for activity at different conditions, it circumvents the need for detailed knowledge of the protein structure, or understanding of protein stability. However, for those well acquainted with the art of protein stability and stabilization it is possible to design more stable proteins by knowledge-based protein engineering. One attractive way to stabilize a specific protein by knowledge-based protein engineering is to graft structural motifs that is known to be stabilizing from one protein homolog to the protein homolog that is to be stabilized, of which there are numerous examples in the literature [10,11]. Two proteins are considered to be homologous if they have identical amino acid residues in a significant number of sequential positions along the polypeptide chain. However, as is text book knowledge in protein chemistry, the three dimensional structure is much more conserved than sequence and it is often found that proteins with very low sequence identity still have similar function and similar three-dimensional structures[12]. Thus, members of such families are also considered to be homologous even though polypeptide sequence identities are not statistically significant, only structurally or functionally significant. Furthermore, homologous proteins always contain a core region (structurally conserved regions) where the general folds of the peptide chains are very similar. That is, the scaffold of even distantly related homologous proteins with low sequence identity have similar structure. It is these relationships that make it possible to transfer stabilizing amino acid combinations or motifs between structurally homologous proteins if there is three dimensional structural data available. Structural data can originate from X-ray crystallography, nuclear magnetic resonance spectroscopy or model building. If two such structures of homologous proteins are superimposed, one with stabilizing interactions of interest (the template) and the other to be stabilized (the target), the three dimensionally structurally equivalent position of stabilizing amino acids to be changed can be identified in the target structure.

One way of reducing the freedom (i.e. entropy) of the unfolded state and thus place the unfolded state on a higher energy level is to introduce covalent links between parts of the protein. This can be done by changing the original amino acids to cysteines which are able to form covalent disulfide bridges (S—S) if the thiol groups of the two amino acid side chains are correctly placed in space. To design such bridges is however not trivial since the geometry of an unstrained —$CH_2$—S—S—$CH_2$— bridge in proteins is limited to rather narrow conformational constraints, and deviations from the geometrical constraints will introduce strains into the folded structure. However, because of the geometrical constraints, identification of disulfide bridges are particularly amenable for homology modeling to identify amino acid positions to alter to cysteines in order to introduce disulfide bridges in homologous proteins, of which there are numerous examples of in the literature[13,14]

Although this method has a limited rate of success since the replacement of the wild type amino acid and the introduction of a disulfide bridge will often lead to loss of favorable interactions or strain in the folded state, it will lead to a larger thermodynamic stability ($\Delta G_{FU}$) if the folded state is unaffected (See FIG. 4).

Further, if the introduced disulfide bridge brings together parts of the protein that normally are in close contact during early stages of the folding event, it will not affect the folding pathway and will thus only increase the thermodynamic stability and possibly the rate of folding (under the prerequisite that the energy level of the folded state is unaffected). If however the introduced disulfide bridge brings parts of the protein together, that during normal folding does not interact early in the folding event, this will lead to that the protein likely needs to fold via an alternative route that has a transition state of higher free energy. Under the prerequisite that the energy level of the folded state is unaffected, this will lead to that the activation energy for unfolding ($E_{A,\ unfolding}$) will become higher and thus the unfolding rate will be slower and the lifetime of the protein will be increased. If this can be accomplished, an ideal protein, with both a high thermodynamic stability (and possibly increased melting temperature) and a high kinetic stability, is constructed (See FIG. 5).

Besides being potentially able to increase both the thermodynamic and the kinetic stability of proteins, the stabilization is of entropic origin by restricting the freedom of the unfolded state by incorporation of a covalent bond (disulfide bridge). Thus, enthalpic stabilizing interactions by introducing disulfide bridges will not display a strong temperature dependence, which can otherwise weaken or strengthen e.g. hydrogen bonds, salt bridges, ionic bonds or hydrophobic effects. In addition, this also means that the stabilization will be less influenced also by other characteristics of the surrounding media, such as polarity and ionic strength etc, and the relative increase in stability will be maintained also in media other than buffered aqueous solutions.

From the above it can be presumed that to increase the physical stability of a protein even more, one simply adds more disulfide bridges. However, this is not uncomplicated for several reasons. Firstly, the introduction of even a single stabilizing disulfide bond is challenging, since often what is gained in energy difference by decreased entropy of the unfolded state is often also lost in enthalpic energy in the folded state, because of lost non-covalent interactions, or strain introduced into the structure so that the $\Delta G_{FU}$ of the engineered protein is the same or even less than that of the wild type protein (i.e. thermodynamically destabilized). Thus, introducing two or more disulfide bridges might increase or decrease the stability of the protein. Secondly, with two disulfide bridges present, the folding pathway of the protein could be blocked, so that the protein is no longer able to fold into its native active form. Thirdly, when more than two cysteines are introduced in a protein there is a high risk that the cysteines make disulfide bonds with the wrong partner during synthesis or folding. This will always lead to an inactive protein as it will not be able to find its folded active conformation. This is also especially important during production of heterologous (e.g. mammalian) proteins with multiple disulfide bonds in recombinant systems (e.g. bacteria) as the formation of correct or native disulfide bonds in such systems is very inefficient, often leading to low yield of production of functional enzymes.

SUMMARY OF THE INVENTION

Since there are no naturally occurring carbonic anhydrases meeting the requirements that need to be met to be used in an enzyme based bioreactor to capture $CO_2$, there exists a need in the art for development of engineered carbonic anhydrases that meet the expected requirements and which are simple and economical to produce, have a high catalytic activity, have a high physical stability and a long life time under various conditions.

The aim of the present invention is therefore to solve the problems and disadvantages described above by providing a carbonic anhydrase which is simple and economical to produce, has a high catalytic activity, a high physical stability as determined by thermodynamic, thermal and kinetic stability and a long life time under various conditions.

This is achieved according to the present invention by means of an isolated polypeptide having carbonic anhydrase activity, the sequence of which corresponds to modified human carbonic anhydrase II, wherein the polypeptide comprises the mutations A23C, S99C, L202C, C205S and V241C relative to wild type human carbonic anhydrase II having the amino acid sequence of SEQ ID NO: 9, has increased physical stability compared to wild type carbonic anhydrase II and further comprises disulfide bridges between C23 and C202 and/or between C99 and C241.

According to one embodiment the isolated polypeptide having carbonic anhydrase activity has a thermodynamic stability increased by 23.5 kJ/mol compared to wild type carbonic anhydrase II.

According to another embodiment the isolated polypeptide having carbonic anhydrase activity has a melting point increased by 18.5° C. compared to wild type carbonic anhydrase II.

In a further embodiment the isolated polypeptide having carbonic anhydrase activity has an activation energy of unfolding increased by 25 kJ/mol compared to wild type carbonic anhydrase II.

In one embodiment the isolated polypeptide having carbonic anhydrase activity has a rate of unfolding in water at 21° C. that is about 22.000 times slower compared to wild type human carbonic anhydrase II.

According to one embodiment the isolated polypeptide having carbonic anhydrase activity has a half-life of 86 days at 60° C., 8 days at 65° C. and 1.6 days at 70° C.

According to another embodiment the isolated polypeptide having carbonic anhydrase activity maintains its increased physical stability compared to wild type carbonic anhydrase II in aqueous solutions of ethanol amines, comprising methyldiethanolamine (MDEA), monoethanolamine (MEA), diethanolamine (DEA), and aminoethoxyethanol.

According to a further embodiment the isolated polypeptide having carbonic anhydrase activity has the sequence according to SEQ ID NO: 8.

The aim of the present invention is further achieved by a method of increasing the physical stability of carbonic anhydrases (EC 4.2.2.1) selected from the superfamily of naturally occurring or modified α-carbonic anhydrases, comprising insertion of a combination of two stabilizing disulfide bridges at the three dimensionally equivalent or sequentially homologous positions to C23, C99, C202 and C241 in SEQ ID NO: 8, equivalent to positions A23, S99, L202 and V241 in human carbonic anhydrase II.

The present invention also relates to a construct comprising a polypeptide according to the present invention, operably linked to one or more control sequences that direct the production of the polypeptide in an expression host.

In one embodiment the present invention relates to a recombinant expression vector comprising the construct according to the invention.

The aim of the present invention is further achieved by means of a recombinant host cell comprising the construct according to the invention or the recombinant expression vector according to the invention.

The aim of the present invention is further achieved by use of an isolated polypeptide having carbonic anhydrase activity according to the present invention for extraction of carbon dioxide from a carbon dioxide containing medium.

According to another embodiment the carbon dioxide containing medium is a gas.

In one embodiment the gas is a flue gas, biogas, vent gas, or natural gas.

In another embodiment the carbon dioxide containing medium is a liquid.

In a further embodiment the carbon dioxide containing medium is a multiphase mixture.

According to one embodiment the extraction of carbon dioxide from a carbon dioxide containing medium takes place in a bioreactor.

The present invention further relates to a method of preparing an isolated polypeptide of SEQ ID NO: 8, comprising acceleration of the formation of disulfide bridges by incubation of the polypeptide at elevated temperatures of 25-60° C. in the presence of an oxidizing agent at a pH of 7-10.

Further, the present invention relates to an isolated polynucleotide having a sequence which encodes for a polypeptide according to the present invention.

According to one embodiment the isolated polypeptide has at least 75% remaining $CO_2$ hydration activity compared to pseudo-wild-type HCA II.

In one embodiment the isolated polypeptide has a thermodynamic stability of 54 kJ/mole.

In another embodiment the isolated polypeptide has a melting point of 77.5° C. after incubation for 15 min.

In a further embodiment the isolated polypeptide has a remaining $CO_2$ hydration activity of 100% after incubation for 15 min at 70° C.

In another embodiment the isolated polypeptide has a remaining $CO_2$ hydration activity of at least 20% after incubation for 15 min at 70-95° C.

According to another embodiment the isolated polypeptide has a remaining $CO_2$ hydration activity of 100% after incubation for 2 h at 65° C.

According to a further embodiment the isolated polypeptide has an activation energy of unfolding of 121 kJ/mole.

In a further embodiment the isolated polypeptide has a rate of unfolding in water at 21° C. of $4.2 \times 10^{-9}$ $min^{-1}$.

According to a further embodiment the isolated polypeptide has at least 95% identity with the amino acid sequence of SEQ ID NO: 2 or SEQ ID NO: 4 or SEQ ID NO: 6 or SEQ ID NO:8.

According to another embodiment the isolated polypeptide has at least 98% identity with the amino acid sequence of SEQ ID NO: 2 or SEQ ID NO: 4 or SEQ ID NO: 6 or SEQ ID NO: 8.

BRIEF DESCRIPTION OF THE DRAWINGS

(FIG. 7A), 65° C. (FIG. 7B) and 70° C. (FIG. 7C) for SEQ ID NO:2 (○), 4 (■), 6 (□) and 8 (●). Note that SEQ ID NO 2 is only measured at 60° C. as it is instantly inactivated already at this temperature (FIG. 7A) and that SEQ ID NO: 4 is only measured at 60 and 65° C. (FIGS. 7A and 7B). The only variant having an appreciable life time at all temperatures is the polypeptide of SEQ ID NO: 8.

DETAILED DESCRIPTION OF PREFERRED EMBODIMENTS OF THE INVENTION

Figure 1:
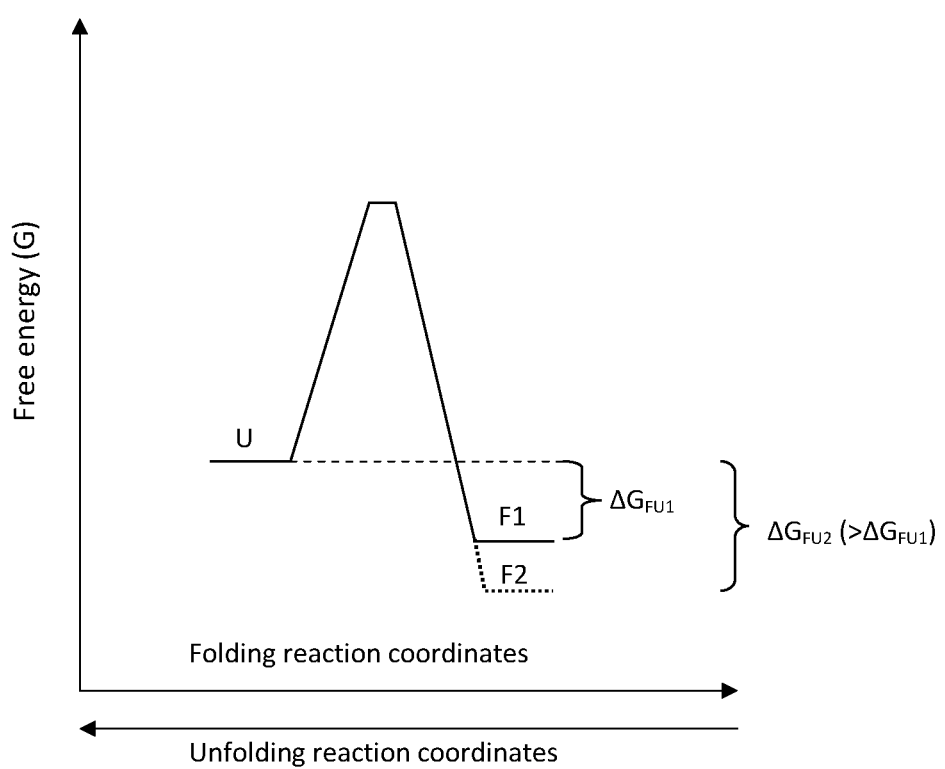
FIG. 1 is a graph illustrating the definition of difference in free energy, between the unfolded state (U) and the native folded state (F) of a protein ($\Delta G_{FU1}$). The graph further illustrates how the thermodynamic stability can be increased by stabilizing the folded state ($\Delta G_{FU2}$).
Figure 2:
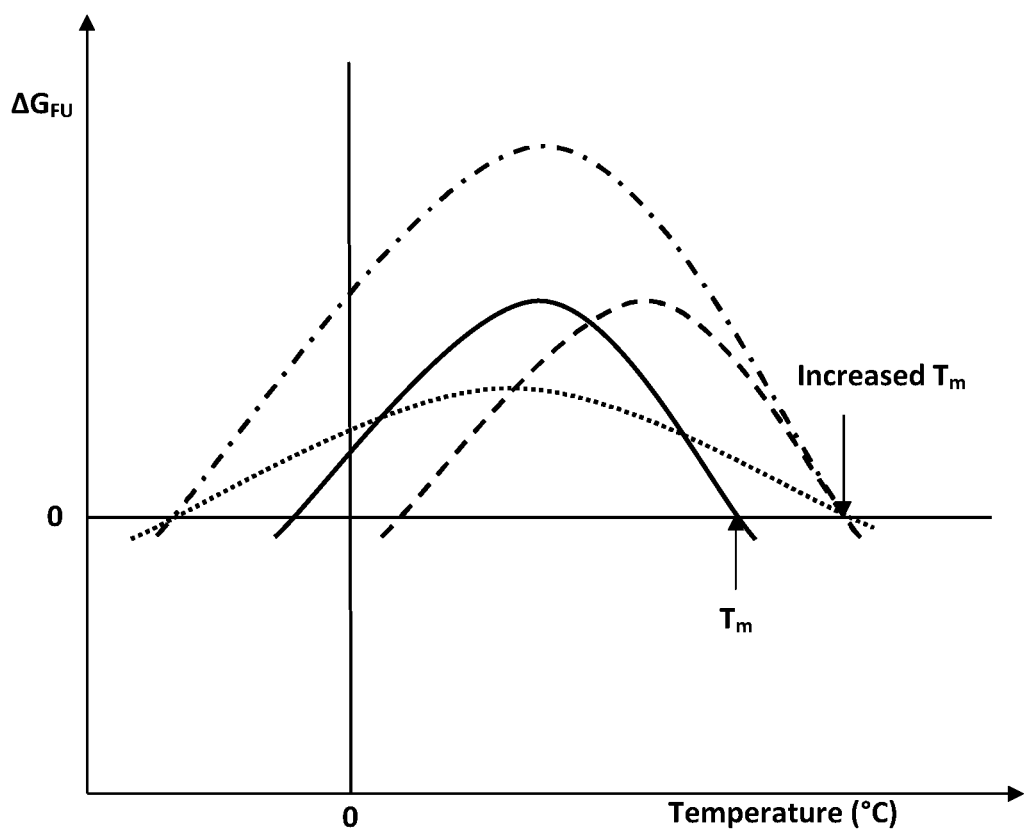
FIG. 2 illustrates the relationship between thermodynamic and thermal stability and that knowledge about the thermodynamic stability at a single temperature does not give any information about the melting temperature ($T_m$) of a protein. The $\Delta G_{FU}$ (T) function of a hypothetical thermolabile protein (—) with its melting temperature ($T_m$) and the possible increase in $T_m$ by up shifting (— —), right shifting (- - -) and flattening (·····) of the $\Delta G_{FU}$(T) function (adapted from ref. 8).
Figure 3:
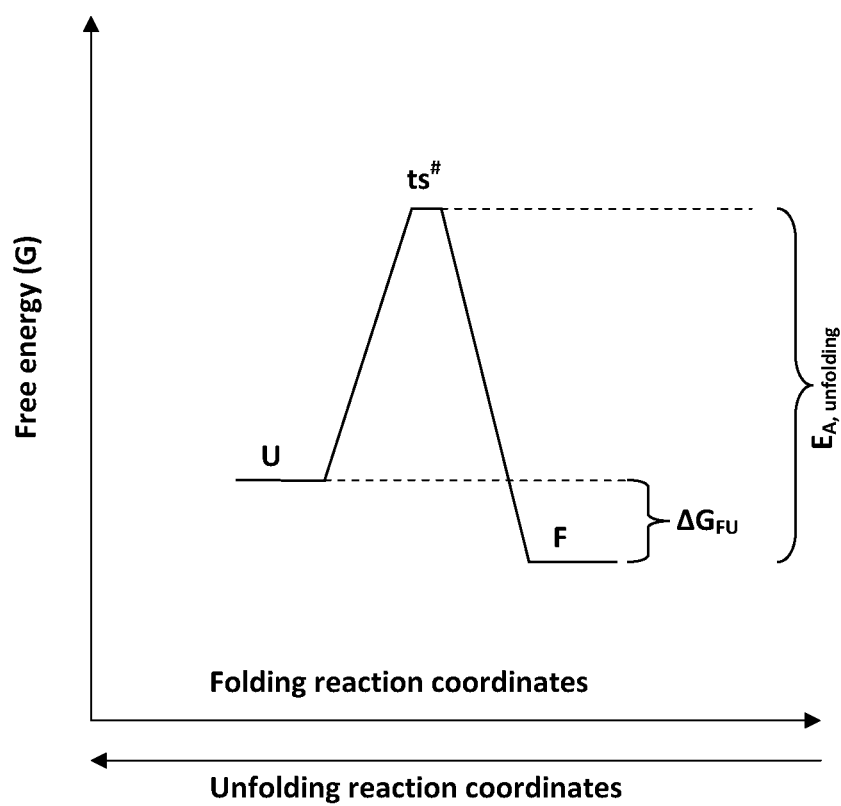
FIG. 3 is a graph illustrating the definition of activation energy of unfolding ($E_{A,\ unfolding}$) of a protein determined by the difference in free energy between the folded state (F) and the transition state ($ts^{\#}$) on the unfolding pathway.
Figure 4:
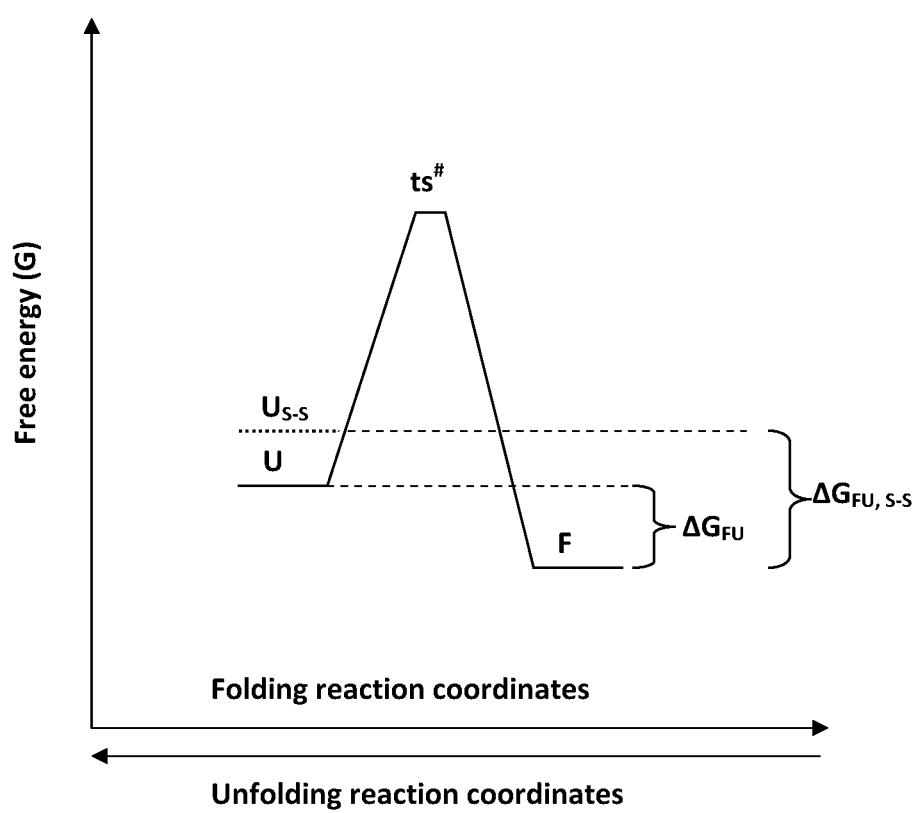
FIG. 4 is a graph illustrating how the thermodynamic stability ($\Delta G_{FU}$) for a protein is increased by restricting the freedom of the unfolded state by incorporation of a disulfide bridge ($U_{S-S}$), thus placing the unfolded state on a higher energy level.
Figure 5:
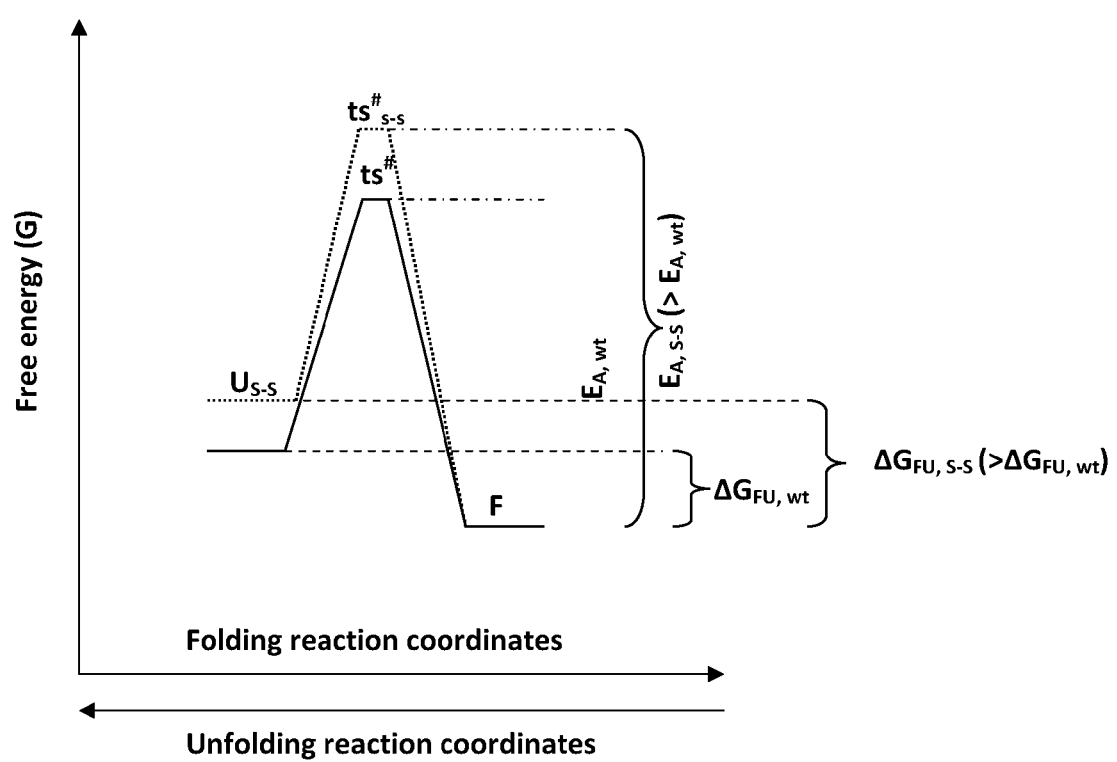
FIG. 5 is a graph illustrating the resulting increase in both thermo-dynamic stability ($\Delta G_{FU,\ S-S}$) and activation energy for unfolding ($E_{A,S-S}$), for a protein with a disulfide bridge inserted at positions that affect both the freedom of the unfolded state as well as the folding pathway and thereby the transition state (·····). Comparison is made with an unmodified reference wild type (wt) protein (—).
Figure 6:
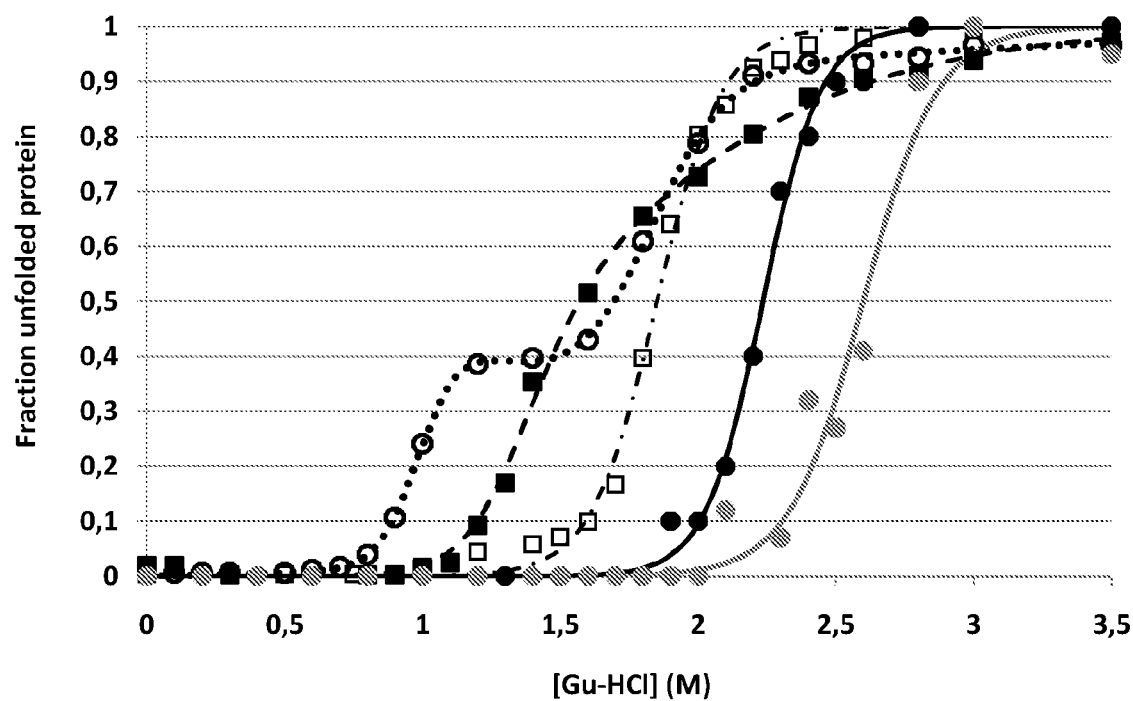
FIG. 6 is a graph illustrating the enzyme variants resistance to unfolding in a denaturing agent as fraction of unfolded protein as a function of Gu-HCl concentration for SEQ ID NO: 2 (○), 4 (■), 6 (□) and 8 incubated over night (✶) and SEQ ID NO: 8 incubated 2-5 days (●).

One aspect of the present invention is to provide an enzyme that has a high enough physical stability to make bioreactors, that are designed and capable of extracting $CO_2$ from a $CO_2$-containing medium, practical and economically feasible.

The present disclosure provides an engineered, highly efficient, human carbonic anhydrase II variant that has an increased physical stability as determined by thermodynamic, thermal and kinetic stability as well as prolonged life time.

The stabilized human carbonic anhydrase II according to the present invention has a thermodynamic stability increased by 23.5 kJ/mol.

The present invention further provides an engineered human carbonic anhydrase II that is heat-stable and is able to catalyze the hydration of $CO_2$ at normal and elevated temperatures over long periods of time. The heat stability of the present invention provides a carbonic anhydrase that has a melting point of 77.5° C. and maintains 100% $CO_2$ hydration activity for at least 15 min at 70° C. and more than 20% residual $CO_2$ hydration activity at 95° C. for at least 15 min.

The present invention also provides an engineered kinetically stabilized human carbonic anhydrase II that has an activation energy for unfolding ($E_{A,\ unfolding}$) increased by 25 kJ/mol and a rate of unfolding ($k_U$) at ambient temperature that is about 22 000 times slower than the wild type enzyme.

The present disclosure further provides an engineered human carbonic anhydrase II that maintains its relative stabilization properties in relation to the wild-type enzyme also in solutions other than buffered aqueous solutions e.g. ethanolamine solutions.

The present invention also provides a method to economically and effectively produce the engineered human carbonic anhydrase II according to the present invention.

The present invention further provides polynucleotides encoding the wild-type and the engineered human carbonic anhydrase II according to the invention.

The present invention relates to a genetically engineered variant of the enzyme human carbonic anhydrase II having the amino acid sequence according to SEQ ID NO: 8, having substantially increased physical stability, as defined by increased thermal, thermodynamic and kinetic stability, and as compared to those of its parent enzymes having the amino acid sequence of SEQ ID NO: 2, 4 and 6. The nucleotide sequences corresponding to SEQ ID NO: 2, 4, 6 and 8 are shown in SEQ ID NO: 1, 3, 5 and 7, respectively. The increased physical stability provides the enzyme properties that allows the enzyme to be used, with an increased life-time, at elevated temperatures (i.e. higher than 37° C.) and in media other than buffered aqueous solutions (e.g. in methyldiethanolamine solutions).

Furthermore, the combination of SEQ ID NO: 2, 4 and 6 leads to the properties of SEQ ID NO: 8 that allows it to be produced in an economically viable way. One aspect of the invention is the use of stable carbonic anhydrases as catalysts in bioreactors for capture and sequestration of $CO_2$ from $CO_2$-containing gases, liquids or multiphase mixtures. The present invention is of particular importance when a prolonged life-time is desired and/or when the temperature of the $CO_2$-containing medium is above the melting point of naturally occurring or commercially available carbonic anhydrases. The present invention is additionally useful both for sequestration (hydration) of $CO_2$ and subsequent recovery of bicarbonate (dehydration) of the previously sequestered $CO_2$.

Definitions

"Carbonic anhydrase" and the abbreviation "CA" is used interchangeably to refer to a polypeptide having enzymatic E.0 4.2.1.1 activity and that is capable of catalyzing the inter-conversion of carbon dioxide and water to bicarbonate and a proton.

"Human carbonic anhydrase II" and "HCA II" is used interchangeably to denote the iso-form 2 variant of human carbonic anhydrase II. Wild type human carbonic anhydrase II has the amino acid sequence defined in SEQ ID NO: 9 (GenBank accession number NM 000067.2).

"Wild-type" or "naturally occurring" refers to the form of polypeptide or polynucleotide sequence that can be found in nature and has not been intentionally modified by human manipulation.

"Pseudo-wild-type human carbonic anhydrase II" ("HCA $II_{pwt}$") refers to a variant of human carbonic anhydrase II with characteristics indistinguishable from the wild type human carbonic anhydrase II with the naturally occurring cysteine in position 205 exchanged by genetic manipulation to instead code for the amino acid serine (C205S). Conventional denotation of human carbonic anhydrase iso-form sequences sometimes refers to positions relative to the positions in human carbonic anhydrase I and numbering can thus differ between different publications. However, unless otherwise stated all positions defined in this text refers to the sequences and positions as defined in SEQ ID NO: 1-8.

"Modified" polypeptides according to the invention involves polypeptides having more mutations, truncated variants of the polypeptides, and polypeptides having one or more amino acids added at the N- or C-terminal part of the polypeptide.

EXAMPLES

Example 1

Selection of Mutation Positions

The positions chosen for mutation and introduction of cysteines were based on the findings of two earlier variants of HCA $II_{pwt}$. Although not a valid measure of physical stability[15], for one variant (SEQ ID NO: 4) the midpoint of denaturation in increasing concentrations of a chemical denaturant (guanidine hydrochloride) was increased[16]. In another variant (SEQ ID NO: 6) the thermodynamic stability was increased at ambient temperature (23° C.)[17]. In these two individually engineered disulfide bridge variants of HCA $II_{pwt}$, cysteine in position 99 makes a disulfide bridge with cysteine in position 241 in one variant (SEQ ID NO: 4) and in the other variant (SEQ ID NO: 6) cysteine in position 23 makes a disulfide bridge with cysteine in position 202. However, all other important parameters concerning stability for these variants were unknown. Since the following information cannot simply be deduced from knowing the midpoint concentration of unfolding for one component (SEQ ID NO: 2) or the thermodynamic stability at ambient temperatures of the other component (SEQ ID NO: 6), the thermodynamic stability, the melting point, the stability in 30% ethanol amine solution, the kinetic stability, the unfolding rates and the lifetime at elevated temperatures of both the individual variants (SEQ ID NO: 4 and 6) were determined according to the following examples. From the collective information gained for the individual variants (SEQ ID NO: 4 and 6) in example 6-10 in this document, it is understood that both variants individually possess properties that are beneficial for carbonic anhydrases to be used in an industrial process designed to capture $CO_2$. Thus, a combination of the two variants could tentatively lead to an enzyme variant with several of the necessary properties enhanced. However, as can be understood from the background art, this cannot be acclaimed without the necessary design of a combined variant and the characterization thereof.

Furthermore, a combination of the two disulfide bridges could very well also lead to that the protein can no longer fold or the cysteines make disulfide bonds with the wrong partner and thereby fold to a non-native state. For one of the variants (SEQ ID NO: 6) it was also earlier found that an out of the ordinary chemical method was needed to form the disulfide bridge under an acceptable time scale, which would hamper the large scale production of the enzyme[16]. For the efficient large-scale production of the enzyme the earlier proposed methods would be hard to implement to an economically feasible industrial production process of the enzyme. Thus, based on the experimental findings of the two single-disulfide variants in this document, a novel double-disulfide variant (SEQ ID NO: 8) was designed (example 2), produced (example 3-5) and characterized with regards to important properties such as activity, physical stability and lifetime (example 6-11).

Example 2

Site-directed Mutagenesis of HCA II

All variants were produced by the same methods. As a template for further modifications, a nucleotide (SEQ ID NO: 1) coding for a well known variant of HCA II with the only cysteine in the polypeptide sequence at position 205 (SEQ ID NO: 2) replaced with a serine, was used[18]. The use of this variant prevents faulty disulfide bridges from being formed between any introduced new cysteine and the otherwise single naturally occurring cysteine in position 205. This variant of HCA II has further properties that are indistinguishable from the wild type HCA II and is therefore identified as a pseudo-wild-type human carbonic anhydrase II (HCA $II_{pwt}$). The nucleotide sequence coding for HCA $II_{pwt}$ was cloned into the plasmid pACA, a vector for T7-RNA polymerase-directed expression. The production of T7 RNA polymerase is in turn under control by a lac promoter, thus production of the cloned HCA II protein can be activated by addition of lactose or analogs such as IPTG. The plasmid was maintained in a laboratory expression strain of *E. coli* (BL21/DE3). Plasmids were prepared by using the Qiagen plasmid preparation kit according to the manufacturer's instructions. Mutagenesis oligo-nucleotides were designed and ordered to specification from DNA technology AS (Denmark). The HCA $II_{pwt}$ nucleotide sequence, contained in the purified plasmids, was thereafter subject to site-directed mutagenesis using the aforementioned DNA oligomers and the QuickChange® site-directed mutagenesis kit from Stratagene. After purification of the treated plasmids, aliquots of the plasmids was sent for sequencing (GATC Gmbh, Germany) for verification of correct desired sequence and mutations. After verification the plasmids was used to transform a new set of BL21/DE3 cells which were grown to a cell density of approx. OD 1 at $A_{660}$ in 20 ml 2×LB medium. The cells were transferred in aliquots of 500 μL to Eppendorf tubes and mixed with 500 μL 50% glycerol and frozen in liquid nitrogen. The *E. coli* stocks were thereafter stored at −70° C.

Example 3

Protein Production

All variants were produced by the same methods. 2×15 mL of over-night cultures of 50 mL of transformed BL21/DE3, containing plasmids carrying the mutated HCA $II_{pwt}$, and grown in LB medium at 37° C., was transferred and used to inoculate 2×1.5 L of LB medium in shake bottles. The cells were allowed to grow at 37° C. to a cell density of approx. OD 0.8 at $A_{660}$ and were then supplemented with IPTG and $ZnSO_4$ to a final concentration of 1 mM, respectively and the cells were left to produce the protein over night. The cells of the culture broths were sedimented by centrifugation at 3.000×g and the supernatant was discarded. The cells were resuspended in 40 mL of 10 mM tris-$H_2SO_4$, pH 9.0. The cell suspension was thereafter subjected to ultrasonication to break the cell walls and release the cell content. The cell suspension was thereafter centrifuged at 10.000×g for 30 min and the supernatant containing the produced mutated HCA $II_{pwt}$ was collected. The pH of the supernatant was adjusted to an approx. pH of 9 with tris base. The supernatant was mixed with approx. 10 mL of an affinity gel for HCA II (BioRad CM agarose with a sulfonamide coupled to the matrix) and allowed to stand for 30 min before being applied to a chromatography column. The gel was washed with several bed volumes of 10 mM tris-$H_2SO_4$, pH 9.0 under monitoring of the $A_{280}$. When no more change in $A_{280}$ could be detected the protein was eluted with 10 mM tris-$H_2SO_4$, pH 7.0 and 0.5 M azide. The eluate was collected and transferred to dialysis tubes with a molecular weight cut-off of 10 kDa (Millipore) and then dialyzed against 5×10 L of dialysis buffer (10 mM tris-$H_2SO_4$, pH 7.5) with at least 8 h between each change of buffer. The dialyzed protein solutions were then collected and concentrated in centrifugation tubes with a molecular cut-off of 10 kDa.

Concentration of the protein sample was determined by $A_{280}$ measurement using an extinction coefficient of $\epsilon_{280}$=55 400 $M^{-1}$ $cm^{-1}$. The protein sample was further analyzed for purity by overloading of protein sample (10 pg per well) onto a SDS-PAGE. After the SDS-PAGE run the proteins in the gel were stained with commassie brilliant blue. For each produced protein sample it was found that no other protein band could be visually detected. Thus, since the proteins were considered to be pure the mutated variants of HCA II could be subject to further analysis.

Example 4

Detection of Free Cysteines

All variants containing cysteines were analyzed by the same methods. Free cysteines, i.e. non-productive cysteines that had not formed a cystine residue with its expected partner and thus had not formed a stabilizing disulfide bridge, was detected by 7-chloro-4-nitrobenzofurazan (NBD-CI). Protein, tris-$H_2SO_4$ pH 7.5 and guanidine hydrochloride (Gu-HCl) were mixed to a final concentration of 17.1 μM, 0.1 M and 5 M, respectively. Free cysteines were detected with a time scan of 30 min at 420 nm using a spectrophotometer (Hitachi U-2001) after addition of a tenfold excess of NBD-CI (171 μM). As a reference, a sample of HCA $II_{pwt}$ (that has no cysteine amino acid residue) was run. If there are free cysteines, the NBD-CI will react with the thiol group and form a cysteine-NBD moiety that absorbs light in the visual wavelength (turns yellow). With an extinction coefficient of $\epsilon_{420}$=13 000 $M^{-1}$ $cm^{-1}$ for the cysteine-NBD moiety, one free cysteine per protein will give an absorbance $A_{420}$ of 0.22 at the used concentration of protein after the reaction, and four free cysteines will thus give an absorbance $A_{420}$ of 0.88. The only disulfide variant that did not show increase of absorbance at 420 nm after the reaction was the single disulfide bridge variant SEQ ID NO: 4 which thus had no free cysteines and a single disulfide bond fully formed. The other single-disulfide variant (SEQ ID NO: 6) was, as earlier found, not able to spontaneously form its disulfide bridge[16, 17]. More importantly, it was subsequently found that the novel double-disulfide variant (SEQ ID NO: 8) also had about 50% of free cysteins (2 out of 4 cysteines not forming a disulfide bridge). Most likely, this indicates that one disulfide bridge had formed spontaneously, whereas the other disulfide bridge was not formed during production of the enzyme of SEQ ID NO: 8. Thus, a method to form the missing disulfide bridge needed to be developed.

Example 5

Formation of Disulfide Bridges of SEQ ID NO: 6 and 8

Due to low resistance of the reduced form towards unfolding in guanidine hydrochloride ($C_{m, FU}$ of 0.7 M Gu-HCl)[17], the disulfide bridge of SEQ ID NO: 6 was formed by a chemical method as has previously been described in the literature[16], resulting in a protein with both cysteines reacted in a correct disulfide bridge and with a retained native and active conformation. However, the double-disulfide bridge variant of SEQ ID NO: 8 had only one out of two disulfide bridges formed. Most likely, it was the disulfide bridge of SEQ ID NO: 4 that had formed and the disulfide bridge of SEQ ID NO: 6 that had not formed, analogously to the behavior of the individual disulfide bridge variants. Nevertheless, regardless of which of the two disulfide bridges that had formed, each will individually lead to a higher thermal stability of the protein (see example 9). Thus, instead of using the earlier described chemical method to increase the structural flexibility to facilitate for the cysteines to find each other, the formation of the second disulfide bridge in SEQ ID NO: 8 could be accomplished by allowing the reaction to take place at elevated temperatures.

Therefore, an alternative scheme to the chemical method used to form the disulfide bridge of SEQ ID NO: 6 was developed for the double-disulfide bridge variant of SEQ ID NO: 8. Since the melting point of the least stabilized variant (SEQ ID NO: 4) with a formed disulfide bridge is increased by 7.5° C. and is unaffected by incubation at temperatures <55° C. (see example 9), the double disulfide variant of SEQ ID NO: 8 could effectively be incubated at 50° C. to induce formation of the second disulfide bridge donated from SEQ ID NO: 6. For the purpose of verifying this approach an experimental assay was designed. Two stock solutions containing 85.5 µM of protein (SEQ ID NO: 8 with only one disulfide bridge formed) in 50 mM tris-$H_2SO_4$ pH 8.5 supplemented with a 100 fold concentration of oxidized dithiotreitol (DTT) was prepared. One solution was incubated at room temperature whereas the other was incubated in a heated cabinet at 50° C. At certain time points aliquots of the stock solutions were withdrawn and measured for free cysteines as described in example 4. It was found that by incubating the sample at 50° C. this method yielded 100% disulfide bridge formation of SEQ ID NO: 8 within 24 hours. At this time the sample incubated at room temperature had only formed approx. 20% of the disulfide bridges. The samples were further analyzed by SDS-PAGE which revealed that no dimers had been formed during the thermal process, indicating that correct disulfide bridges had been formed. In terms of applicability of the enzyme of SEQ ID NO: 8 this is a very important result as it makes the large-scale production of the variant feasible. Partly because, as compared to the earlier described chemical method, less amount of costly chemicals is needed since no addition of Gu-HCl is necessary in the process.

Furthermore, the completed enzyme product does not need down stream processing to be cleaned from the denaturing agent Gu-HCl. Yet more, the reaction rate with SEQ ID NO: 8 and the described "thermal" method is faster (24 h for 100% disulfide bridge formation) than the chemical method as it takes place at elevated temperatures. This can be compared to the rate of disulfide bridge formation in SEQ ID NO: 6 using the earlier described chemical method (100 h for 100% disulfide bridge formation).

Example 6

Stability against Unfolding by Denaturing Agents in Aqueous Solution and in 30% Methyldiethanolamine Aliquotes of 0.85 µM solutions of each of the described HCA II variants of SEQ ID NO: 2, 4, 6 and 8 were incubated in room temperature over night (approx 18 hours) in increasing amount of the denaturant Gu-HCl (0-6 M) in buffered solutions (0.1 M tris-$H_2SO_4$ pH 7.5). For the methyldiethanolamine (MDEA) measurements the solution also contained MDEA at a final concentration of 30%. Fluorescence spectra were recorded for each variant at all Gu-HCl concentrations chosen in a spectrofluorometer (Jobin-Yvon Fluoromax 4). Excitation wavelength was 295 nm and three accumulative emission spectra were recorded for each sample between 310-400 nm. From the spectra the wavelength shift was determined. The data was normalized and the fractional change as a function of Gu-HCl concentration was determined. From this it was determined at what Gu-HCl concentration the midpoint of unfolding ($C_{m, FU}$) occurred for each variant in both media (table 1). For samples incubated in buffered aqueous solution the values for HCA $II_{pwt}$ (SEQ ID NO: 2) and the two single disulfide bridge variants (SEQ ID NO: 4 and 6) reached earlier found values ($C_{m, FU}$ of 1.0, 1.40 and 1.85 M Gu-HCl, respectively). Unexpectedly, the subsequently produced novel SEQ ID NO: 8 variant reached an apparent very high $C_{m, FU}$ of 2.6 M Gu-HCl, which is higher than the sum of each individual stabilizing disulfide bridge (1.0+0.4+0.85=2.25 M GuHCl). This could mean one of two things. Either there were some synergistic effect in the stability making the double disulfide bridge enzyme of SEQ ID NO: 8 in fact more stable against denaturation by Gu-HCl than the sum of stabilization of the two contributing single disulfide bridge variants.

Alternatively, the kinetic stability of SEQ ID NO: 8 was increased so that the rate of unfolding was slower and thus the protein sample of SEQ ID NO: 8 did not reach equilibrium in 18 h. Therefore, the very same samples were incubated for an additional 24 h (total of 42 h) before data was collected again. For SEQ ID NO: 8 it was found that the curve had shifted to lower concentrations and stopped at a $C_{m, FU}$ of 2.25 M Gu-HCl. Thus, although the SEQ ID NO: 8 enzyme was not as resistant to denaturants as the initial result indicated, this is still a considerable increase in stability as determined by $C_m$, FU and compared to SEQ ID NO: 2, 4 and 6. Furthermore, this also proves that the combination of disulfide bridge variants of SEQ ID NO: 4 and 6 is achievable since the protein can still fold and the stability reaches the sum of each individual stabilizing disulfide bridge (2.25 M GuHCl) and thus no stabilizing effects regarding resistance to denaturing agents are lost from combining the two.

The slow equilibration that was found for SEQ ID NO: 8 is a behavior that to our knowledge has not earlier been demonstrated for any earlier variants of HCA II. The behavior implies that the double disulfide variant of SEQ ID NO: 8 has a high kinetic barrier to unfolding. This would then lead to that the unfolding rate of SEQ ID NO: 8 is slower than for each of the individual disulfide bridge variants of SEQ ID NO: 4 and 6, and thus that the equilibrium between the folded and unfolded state takes longer time to reach than for each individual disulfide bridge variant (SEQ ID NO: 4 and 6).

TABLE 1

Midpoint concentration of unfolding in increasing concentration of Gu-HCl

| | SEQ ID NO 2 | SEQ ID NO 4 | SEQ ID NO 6 | SEQ ID NO 8 (INCUBATION 3-5 DAYS) | SEQ ID NO 8 (INCUBATION OVER NIGHT) |
|---|---|---|---|---|---|
| $C_{M,FU\_(H2O)}$ (M Gu-HCl) | 1.0 | 1.4 | 1.85 | 2.25 | 2.6 |
| $C_{M,FU\_(30\% MDEA)}$ (M Gu-HCl) | 0.3 | 0.75 | 1.2 | 1.4 | |

The stability against denaturing agents in 30% MDEA follows the same trend, i.e. SEQ ID NO: 2 has the lowest $C_{m, FU}$ followed by SEQ ID NO: 4, 6 and 8 respectively (see table 1). Thus, this result confirms that although MDEA generally destabilizes the proteins, the relative increase in stability against denaturation in Gu-HCl from introduced disulfide bridges is almost unaffected by the properties of the surrounding media, as earlier described. Therefore, also in 30% MDEA, the protein according to SEQ ID NO: 8 has a considerably higher stability than the HCA $II_{pwt}$ variant (SEQ ID NO: 2) has. Thus, the protein variants of SEQ ID NO: 6 and 8 are more stable even in 30% MDEA than SEQ ID NO: 2 is even in buffered aqueous solution.

Example 7

Thermodynamic Stability in Aqueous Solution

The equilibrium constant data (K) in the transition region, for each enzyme variant, obtained in example 6 was used to calculate the thermodynamic stability of the respective enzyme variant in purely buffered aqueous solution according to the relationship ΔG=−RT ln(K) by the linear extrapolation method[19].

TABLE 2

Thermodynamic stability in buffered aqueous solution at ambient temperature (21° C.).

| Thermodynamic stability | SEQ ID NO 2 | SEQ ID NO 4 | SEQ ID NO 6 | SEQ ID NO 8 (inc. 3-5 days) |
|---|---|---|---|---|
| ΔG$_{(H2O)}$ (kJ/mol) | 30.5 | 39 | 46 | 54 |
| ΔΔG$_{(H2O)}$ (kJ/mol) relative to SEQ ID NO 2 | | 8.5 | 12.5 | 23.5 |

Clearly, the increased resistance of SEQ ID NO: 8 to denaturation by Gu-HCl as judged by $C_{m,\ FU}$ values is an effect of a significantly increased thermodynamic stability. Furthermore, the increase in thermodynamic stability of SEQ ID NO: 8 is slightly larger than the sum of increased stability of SEQ ID NO: 4 and 6 (8.5+12.5<23.5), indicating a small synergistic effect.

Example 8

Activity Assays of Carbonic Anhydrases

Activity assays were used in order to measure the change in enzyme activity in response to changes in conditions (denaturing agents and temperature) to reveal melting temperatures ($T_m$), unfolding rates, kinetic stability and life time at elevated temperatures. Activity assays are also important to establish the absolute activity of the protein variants of SEQ ID NO: 4, 6 and 8, in relation to the pseudo-wild-type enzyme, since what is desired is an as high as possible catalytic activity and efficiency also in the engineered variants.

Several variants of colorometric $CO_2$-hydration activity assays have earlier been described in literature[20, 21, 22] which are all based on the enzymatic reaction which leads to the production of bicarbonate and protons from carbon dioxide and water. Thus, enzymatic activity of carbonic anhydrase will give a faster decrease in pH than the spontaneous reaction and can be monitored if the reaction takes place in a buffer containing the pH indicator bromothymol blue (BTB).

An aqueous stock solution saturated with $CO_2$ was prepared by bubbling ice cooled deionized water with $CO_2$ through a gas diffuser for at least 1 hour prior to use. To monitor the $CO_2$-hydration activity per mg of enzyme, 2 ml of 25 mM veronal-$H_2SO_4$, pH 8.2, containing 20 mg/L of BTB was mixed with 1 ml deionized water and 30 μL of protein (8.5 μM) in a small beaker placed in an ice-bath on top of a magnetic stirrer. All solutions were kept on ice prior to use. The reaction was started by the addition of 2 ml of the $CO_2$ saturated solution to the stirred buffer solution. Simultaneously with the addition of $CO_2$ saturated solution a stop watch was started and the time to reach pH 6.5 was determined by comparison of color to a reference sample containing 2 ml 0.2 M Na-phosphate buffer pH 6.5, 2 ml 25 mM veronal $H_2SO_4$, pH 8.2, containing 20 mg/L of BTB and 1 ml deionized water. The time to reach pH 6.5 was measured for the catalyzed reactions ($t_c$) and for the uncatalyzed blank reactions ($t_b$) and the following equation was used to determine activity units (A.U.) per mg enzyme:

$$A.U./mg = \frac{\left(\frac{t_b}{t_c}\right) - 1}{mg\ enzyme}$$

In all $CO_2$-hydration experiments the amount of enzyme in the activity assay was 7.5 μg. The $CO_2$-hydration activity of the three disulfide variants (SEQ ID NO: 4, 6 and 8) at the conditions of measurement (0° C.) was found to be 105, 82 and 75 percent respectively of the activity of the HCA II$_{pwt}$ variant. Thus, all disulfide bridge variants remain highly active with regards to $CO_2$ hydration.

Example 9

Thermal Stability Assay

For each enzyme variant (SEQ ID NO: 2, 4, 6 and the subsequently produced SEQ ID NO: 8) stock solutions of 8.5 μM enzyme in 10 mM tris-$H_2SO_4$ pH 7.0 were prepared. Aliquotes of 70 μL enzyme solutions was placed in thin-walled PCR tubes. In order to prevent increase in enzyme concentration in the enzyme solutions after incubation, due to evaporation and condensation of liquid in the PCR tube, a PCR thermocycler with a heated top was used (GeneAmp PCR-system 9600, Applied Biosystems). For each enzyme variant and target temperature a sample was placed in the thermocycler which was programmed for constant ramping to the set temperature (55 to 95° C.) and incubated for 15 min or 2 hours. After incubation the samples were allowed to cool to room temperature for 10 min before measurements of the residual enzymatic activity according to example 8. All experiments were performed in duplicates. The resulting residual activity after thermal treatment for 15 minutes and 2 hours is presented in table 3 and 4, respectively. Clearly, all engineered variants have higher thermostability than the pseudo-wildtype enzyme (SEQ ID NO: 2). Furthermore, the variant with the highest thermostability is the constructed double disulfide bridge variant (SEQ ID NO: 8). To calculate the approximate $T_m$ (i.e. the temperature at which 50% residual activity remain) of each variant, data from the 15 min incubation was fitted to a sigmoidal function (TableCurve, Jandel Scientific) and is presented in Table 5.

However, it is important to note that the $T_m$ values obtained are only apparent melting points. Nevertheless, the increase in $T_m$ ($\Delta T_m$) of modified variants (SEQ ID NO: 4, 6 and 8), as compared to HCA II$_{pwt}$ (SEQ ID NO: 2), represents accurate values. The reason for this is that thermal denaturation of the enzymes is not an equilibrium process but is an example of irreversible inactivation where the enzymes aggregate after unfolding at temperatures close to or above their respective melting points. Thus, what is actually monitored in the activity assay is how large population of enzyme molecules that have yet not unfolded and aggregated at the respective temperature. Consequently, in this case of thermal stability, the kinetic stability is as important as the thermodynamic stability in deciding the behavior at elevated temperatures. Thus, in comparison to the other variants, SEQ ID NO: 8 has two striking characteristics. Firstly, it has an exceptionally high melting point of approximately 77.5° C. which is an increase of 18.5° C. compared to the pseudo-wild-type variant, and even higher than the approx. 70° C. of the γ-carbonic anhydrase from *Methanosarcina thermophila*. Secondly, the enzyme of SEQ ID NO: 8 has an apparent residual activity of above 20% at temperatures far beyond its melting point of 77.5° C. This is almost certainly a result of a remarkably high kinetic stability, resulting in that not even incubation for 15 min at 95° C. is enough to completely inactivate all enzyme molecules. Clearly, this is a valuable feature if the enzyme is to be used in e.g. a temperature phased process were the temperature is continuously altered between low and high temperatures since the high kinetic stability of SEQ ID NO: 8 allows the enzyme to survive short bursts of temperatures far beyond its melting temperature.

TABLE 3

Percent remaining $CO_2$-hydration activity after 15 min incubation

| ENZYME VARI- ANT | TEMPERATURE (° C.) | | | | | | | | |
|---|---|---|---|---|---|---|---|---|---|
| | 55 | 60 | 65 | 70 | 75 | 80 | 85 | 90 | 95 |
| SEQ ID NO 2 | 100 | 22 | 2 | 0 | 0 | ND | ND | ND | ND |
| SEQ ID NO 4 | 100 | 100 | 77 | 4 | 0 | 0 | ND | ND | ND |
| SEQ ID NO 6 | 100 | 100 | 100 | 80 | 2 | 1 | ND | ND | ND |
| SEQ ID NO 8 | 100 | 100 | 100 | 100 | 76 | 26 | 24 | 23 | 22 |

TABLE 4

Percent remaining $CO_2$-hydration activity after 2 h incubation

| ENZYME VARI- ANT | TEMPERATURE (° C.) | | | | | | | | |
|---|---|---|---|---|---|---|---|---|---|
| | 55 | 60 | 65 | 70 | 75 | 80 | 85 | 90 | 95 |
| SEQ ID NO 2 | 100 | 2 | 1 | 0 | 0 | ND | ND | ND | ND |
| SEQ ID NO 4 | 100 | 95 | 50 | 1 | 0 | 0 | ND | ND | ND |
| SEQ ID NO 6 | 100 | 100 | 100 | 39 | 0 | 0 | ND | ND | ND |
| SEQ ID NO 8 | 100 | 100 | 100 | 92 | 38 | 7 | 7 | ND | ND |

TABLE 5

Melting points and increase in melting point of enzyme variants

| Enzyme variant | $T_m$ | $\Delta T_m$ |
|---|---|---|
| SEQ ID NO: 2 | 59 | — |
| SEQ ID NO: 4 | 66.5 | 7.5 |
| SEQ ID NO: 6 | 71.5 | 12.5 |
| SEQ ID NO: 8 | 77.5 | 18.5 |

Example 10

Kinetic Stability of Engineered HCA II Variants

In order to determine the unfolding rates ($k_U$) and activation energy for unfolding ($E_{A,\ unfolding}$) of the respective enzyme variant, chemical denaturation was employed. For the unfolding assay each enzyme variant was subjected to increasing concentrations of Gu-HCl, starting from a concentration of 0.2-0.3 M above their respective midpoint concentration of unfolding ($C_{m,\ FU}$, see table 1, example 6) in steps of 0.1 M. For example HCA II$_{pwt}$ with a $C_{m,\ FU}$ of 1.0 M Gu-HCl, was denatured in Gu-HCl concentrations of 1.2, 1.3, 1.4, and 1.5 M Gu-HCl. Stock solutions of Gu-HCl, to reach the final assay concentration, were prepared and protein stock solutions of 0.5 mg/ml were prepared for each enzyme variant. 2.5 μl of enzyme was mixed with 47.5 μl of Gu-HCl to reach the targeted Gu-HCl concentration and a protein concentration of 0.025 mg/ml (8.5 μM). Each protein variant and each Gu-HCl concentration samples were prepared at room temperature (21° C.), from stock solutions, to monitor residual activity after 10 and 30 sec, and 1, 2, 5, 30, 45, and 60 min. Activity measurements were done as described in example 8 (with 30 μl of sample), with the difference that the buffered BTB solution was supplemented with 0.5 mM of the metal chelator EDTA to prevent refolding of enzymes in the assay. Refolding could otherwise occur as both protein and the denaturing agent (Gu-HCl) is diluted in the activity assay. EDTA binds $Zn^{2+}$ which is released from unfolded enzymes and present in solution, and which is necessary for the activity HCA II. Thus, the addition of EDTA to the assay "freezes" the state of the sample so that residual $CO_2$-hydration activity can be measured. When the residual activity is plotted as a function of time for each Gu-HCl concentration the unfolding rate ($k_U$) at that very Gu-HCl concentration can be calculated by fitting the data to a single exponential term according to $y=axe^{-kx}$. To calculate the unfolding rate constant in aqueous solution the natural logarithm of the measured rate constants for the respective enzyme variant is plotted against Gu-HCl concentration and the linearized data is extrapolated to 0 M Gu-HCl (giving the ln $k_U$ at 0 M Gu-HCl). The free energy of activation ($\Delta G^{\#}$), that is, in this case, the free energy of activation for unfolding ($E_{A,\ unfolding}$), can be calculated using the Arrhenius equation, $\Delta G^{\#}=RT[\ln(k_B/h)-\ln(k_U/T)]$, where R is the gas constant, 8.314 J·mol$^{-1}$·K$^{-1}$, $k_B/h$ is the constant 2.08358·10$^{10}$, T is the absolute temperature in Kelvin and $k_U$ is the rate constant for unfolding. The results from the measurements of kinetic stability are presented in table 6.

TABLE 6

Unfolding kinetics data of enzyme variants at 21° C.

| | SEQ ID NO 2 | SEQ ID NO 4 | SEQ ID NO 6 | SEQ ID NO 8 |
|---|---|---|---|---|
| Lnk$_{U,H2O}$ | −9.30 | −14.1 | −12.2 | −19.3 |
| k$_{U,H2O}$ (min$^{-1}$) | 9.1 * 10$^{-5}$ | 7.5 * 10$^{-7}$ | 5.1 * 10$^{-6}$ | 4.2 * 10$^{-9}$ |
| TIMES SLOWER UNFOLDING AS COMPARED TO SEQ ID NO 2 | | 122 | 18 | 22000 |
| $E_{A,unfolding}$ | 96 kJ/mol | 108 kJ/mol | 103 kJ/mol | 121 kJ/mol |
| $\Delta E_{A,unfolding}$ (INCREASE AS COMPARED TO SEQ ID NO 2) | | 12 kJ/mol | 7 kJ/mol | 25 kJ/mol |

For all stabilized disulfide bridge variants (SEQ ID NO: 4, 6 and 8) there is an obvious decrease in unfolding rate ($k_{U\ (H2O)}$) which culminates in the very slow unfolding of the constructed SEQ ID NO: 8 that unfolds 22.000 times slower than the HCA II$_{pwt}$ variant (SEQ ID NO: 2) in aqueous media at 21° C.

What is important is that the enzyme of SEQ ID NO: 8 behaves as a completely new variant of HCA II. SEQ ID NO: 4 was found to confer a high increase in kinetic stability ($\Delta E_{A,\ unfolding}$ of 12 kJ/mol) and a lower increase in thermodynamic stability ($\Delta\Delta G_{FU}$ of 8.5 kJ/mol), and behaves thus as an enzyme with an engineered disulfide bridge with an altered folding pathway and thereby a transition state at a higher energy level. Contrary to SEQ ID NO: 4, the enzyme of SEQ ID NO: 6 was found to have a lower increase in kinetic stability ($\Delta E_{A,\ unfolding}$ of 7 kJ/mol) but possesses a high thermodynamic stabilization ($\Delta\Delta G_{FU}$ of 12.5 kJ/mol). Thus, this variant has an unfolded state placed on an even higher level of free energy. On the other hand it has a folding pathway that is only slightly altered and therefore a transition state with only a slightly higher energy level than for the enzyme of SEQ ID NO: 2. However, for the enzyme of SEQ ID NO: 8 there is both a very high kinetic stabilization ($\Delta E_{A,\ unfolding}$ of 25 kJ/mol) and a very high increase in thermodynamic stability ($\Delta\Delta G_{FU}$ of 23.5 kJ/mol). For the thermodynamic stability the increase is close, although not identical, to the sum of increased stability of SEQ ID NO: 4 and 6. However, the very large increase in kinetic stability is an unpredictable effect that stems from the successful introduction of two disulfide bridges in the enzyme, at positions that forces the protein to fold via an unexplored pathway, which differs from the enzymes of SEQ ID NO: 2, 4 and 6, while at the same time the folding ability and enzymatic activity is retained.

Example 11

Life-time at Elevated Temperatures Assayed by Esterase Activity Measurements

The increased thermal, thermodynamic and kinetic stability of the double disulfide bridge variant of SEQ ID NO: 8 should render it a high life time at elevated temperatures. For practical reasons this was monitored by the esterase activity of the enzyme. Stock solutions of 2.5 mg/ml of each enzyme variant were prepared in 10 mM tris-$H_2SO_4$ pH 7.0 in tubes with screw cap and sealing to prevent evaporation. These were placed in a heated cabinet at the desired temperature (60, 65 or 70° C.) and aliquotes were withdrawn at different time points for measurement of residual esterase activity. Esterase activity was assayed by adding 6 μL of protein sample to 1.44 mL of reaction buffer (50 mM tris-$H_2SO_4$, pH 8.5 with an ionic strength of 0.1 M adjusted with $Na_2SO_4$) in a cuvette. The sample was supplemented with reagent, 60 μL of 30 mM para-nitrophenyl acetate (pNPA) in ice cold acetone, and briefly mixed before esterase activity was measured at 348 nm in a spectrophotometer. The increase in absorbance of the catalyzed reaction was monitored for 60 seconds and the increase in absorbance of a blank reaction (no enzyme added) was then subtracted. The apparent second-order rate constant (k') was calculated according to earlier described methodology[23].

Figure 7:
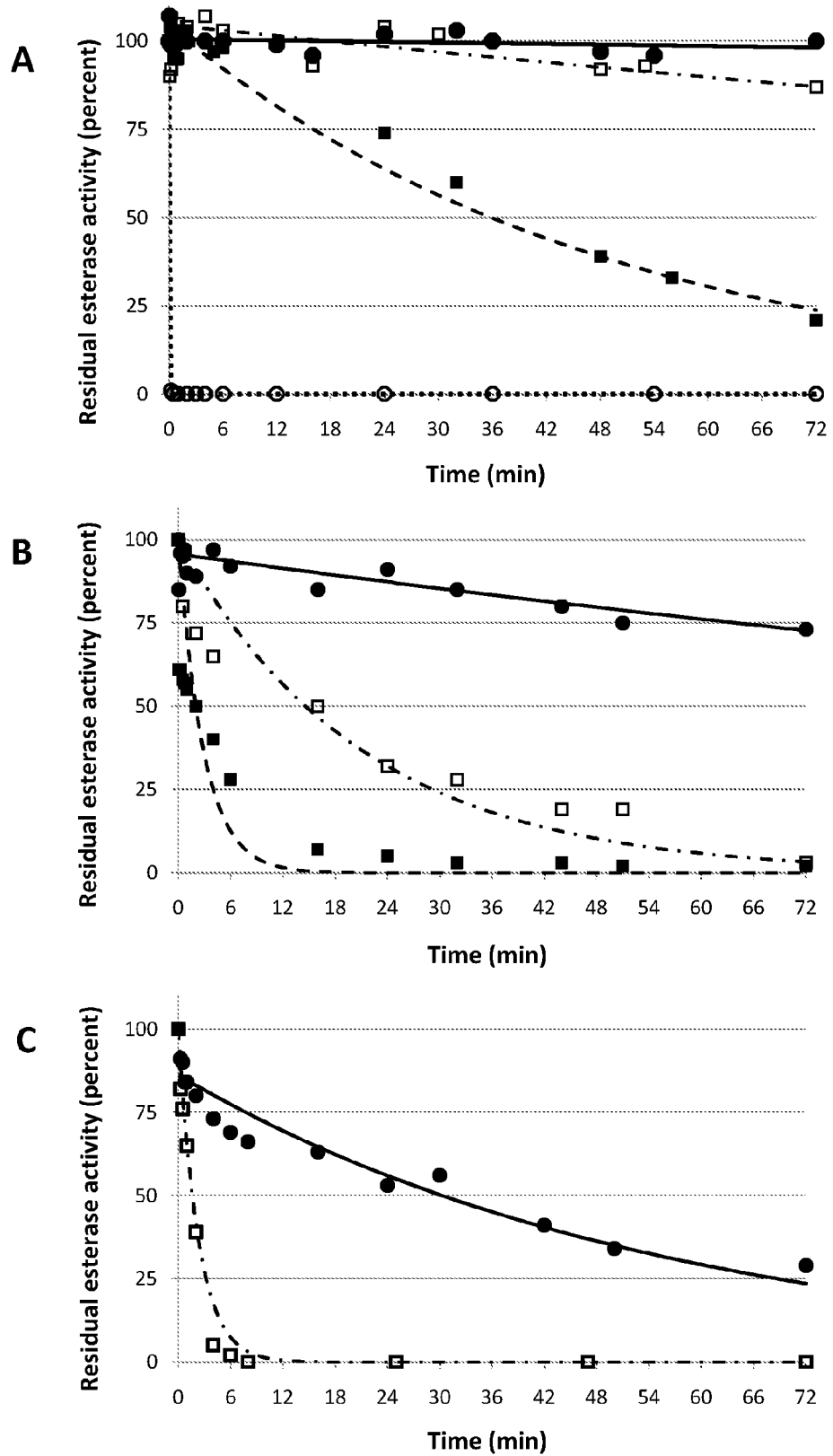
FIG. 7 A-C illustrates the life times at 60° C.

As a time zero reference the esterase activity of each enzyme stock solution was determined before heat treatment. The esterase activity of the three disulfide variants (SEQ ID NO: 4, 6 and 8) at the conditions of measurement (approx. 21° C.) was found to be 99, 86 and 78 percent respectively, compared to the activity of the HCA II$_{pwt}$ variant. Thus, all disulfide bridge variants remain highly active also with regards to the esterase activity and to the approximate same degree as $CO_2$ hydration activity (example 8). The residual activity of each variant at each temperature was plotted against time and fitted to a single exponential term ($y = a \cdot e^{-kx}$) to obtain the rate constant for unfolding for each enzyme variant at the three temperatures. Since the inactivation is a first-order rate process, the half-life ($t_{1/2}$) of each enzyme variant at each temperature can be calculated by $t_{1/2} = \ln 2/k$. The results of the life time experiments are presented in table 7-9 and FIG. 7.

TABLE 7

Percent remaining esterase activity after 15 min incubation

| | TEMPERATURE (° C.) | | |
|---|---|---|---|
| ENZYME VARIANT | 60 | 65 | 70 |
| SEQ ID NO 2 | 1 | 0 | 0 |
| SEQ ID NO 4 | 102 | 61 | 1 |
| SEQ ID NO 6 | 104 | 83 | 82 |
| SEQ ID NO 8 | 99 | 96 | 91 |

TABLE 8

Percent remaining esterase activity after 2 h incubation

| | TEMPERATURE (° C.) | | |
|---|---|---|---|
| ENZYME VARIANT | 60 | 65 | 70 |
| SEQ ID NO 2 | 0 | ND | ND |
| SEQ ID NO 4 | 103 | 50 | ND |
| SEQ ID NO 6 | 104 | 72 | 39 |
| SEQ ID NO 8 | 106 | 89 | 80 |

TABLE 9

Inactivation rate constants ($k_U$), inactivation half time ($t_{1/2}$) and $t_{1/10}$ of enzyme variants at 60-70° C.

| | TEMPERATURE | | | | | | | | |
|---|---|---|---|---|---|---|---|---|---|
| | 60° C. | | | 65° C. | | | 70° C. | | |
| ENZYME VARIANT | $k_U$ (h$^{-1}$) | $t_{1/2}$ (h) | $t_{1/10}$ (h) | $k_U$ (h$^{-1}$) | $t_{1/2}$ (h) | $t_{1/10}$ (h) | $k_U$ (h$^{-1}$) | $t_{1/2}$ (h) | $t_{1/10}$ (h) |
| SEQ ID NO 2 | — | — | — | — | — | — | — | — | — |
| SEQ ID NO 4 | 0.0205 | 35 | 112 | 0.346 | 2 | 6.6 | — | — | — |
| SEQ ID NO 6 | 0.00255 | 272 | 903 | 0.0475 | 15 | 48 | 0.434 | 2 | 5.3 |
| SEQ ID NO 8 | 0.000337 | 2057 (86 days) | 6832 (285 days) | 0.00381 | 182 (8 days) | 604 (25 days) | 0.0180 | 38 (1.6 days) | 127 (5.3 days) |

The increased physical stability, engineered into the double disulfide bridge variant of SEQ ID NO: 8, results in a much slower inactivation rate and thus a much longer life time at increased temperatures than the other variants. At 60° C. the half time of activity inactivation is 86 days for the double disulfide bridge variant of SEQ ID NO: 8 which can be compared to HCA II$_{pwt}$ (SEQ ID NO: 2) which is instantly unfolded and inactivated at the same temperature. Furthermore, the time for the activity to fall down to ⅒ for SEQ ID NO: 8 is approximately 285 days at 60° C. That is, if two different reactors used the same amount of the engineered HCA II of SEQ ID NO: 8 and an enzyme with ⅒ of activity (as for example Cam), respectively, the reactor with SEQ ID NO: 8 would need 285 days to even fall to the low starting value of the Cam reactor. Thus, it is not only the physical stability per se that is important for an enzyme's practicability, but also the activity and efficiency of the protein. Even at 70° C., where all other variants are quickly unfolded and inactivated, the enzyme of SEQ ID NO: 8 has an appreciable slow inactivation and increased life time with a half life of 1.6 days. The ability to withstand temperatures in the range of 60-70° C. with a long life time is an extremely important feature of SEQ ID NO: 8. At for example modern incinerator plants the flue gas cleaning consists of so many steps that the flue gas is cooled down to approx. 60-70° C. before it reaches the smokestack[24]. Thus, any enzyme that is to be used in a $CO_2$-capturing bioreactor at an incinerator plant should preferably also be stable and active in the temperature range of 60-70° C., which is thus fulfilled by the enzyme of SEQ ID NO: 8. Furthermore, the combination of disulfide bridges of SEQ ID NO: 8 has been engineered into an enzyme (HCA $II_{pwt}$) that belongs to the structurally conserved superfamily of α-carbonic anhydrases. To find structurally related proteins, a database search of the three dimensional structure of HCA II (PDB ID 2cba) was executed against the Conserved Domain Database (CDD)[25], which includes alignments of conserved protein domains to known 3-dimensional protein structures in the Molecular Modeling Database (MMDB). The search resulted in 4977 protein sequences with related conserved domains and 438 related solved structures from the α-carbonic anhydrase superfamily. Thus, the combination of the structural motifs of the disulfide bridges between position C23-C202 and C99-C241 in the SEQ ID NO:8 variant of HCA $II_{pwt}$ can be identified and most likely be grafted also into other members of the α-carbonic anhydrase superfamily by homology modeling as earlier described. Indeed, the significantly increased stability of SEQ ID NO: 6 was originally accomplished by homology modeling between HCA II and the distantly related homologous α-carbonic anhydrase from *Neisseria gonorrhoeae* (NGCA, 38.5% sequence identity) which has a naturally occurring disulfide bridge. By homology modeling it was found that the positions for the disulfide bridge in NGCA (sequence positions of C28 and C181) had their three dimensionally structurally equivalent positions in HCA II at the positions A23 and L202. Thus, by homology modeling against a distantly related homologous enzyme a geometrically correct disulfide bridge could be grafted from NGCA into the correct positions in HCA II[17].

REFERENCES

1) Zimmerman, S. A. and Ferry, J. G. (2008). The β- and γ-classes of carbonic anhydrase. *Current pharmaceutical design* 14, 716-721.
2) Alber, B. E., Ferry, J. G. (1994). A carbonic anhydrase from the archaeon *Methanosarcina thermophila*. *Proceedings of the National Academy of Science* 91, 6909-6913.
3) IPCC, 2007: Climate Change 2007: Synthesis Report. Contribution of Working Groups I, II and III to *the Fourth Assessment Report of the Intergovernmental Panel on Climate Change* [Core Writing Team, Pachauri, R. K and Reisinger, A. (eds.)]. IPCC, Geneva, Switzerland.
4) Zimmerman, S. A., Tomb, J.-F., Ferry, J. G. (2010). Characterization of CamH from *Methanosarcina thermophila*, founding member of a subclass of the γ class of carbonic anhydrases. *Journal of Bacteriology,* 192, 1353-1360.
5) Silverman, D. N. and Lindskog, S. (1988). The catalytic mechanism of carbonic anhydrase: Implications of a rate-limiting protolysis of water. *Accounts of chemical research,* 21, 30-36.
6) Ferry, J. G. (2010). The γ class of carbonic anhydrase. *Biochimica et Biophysica Acta,* 1804, 374-381.
7) MacAuley, S. R., Zimmerman, S. A., Apolinario, E. E., Eyilia, C., Hou, Y.-M., Ferry, J. G. and Sowers, K. R. (2009). The archetype γ-class carbonic anhydrase (Cam) contains iron when synthesized in vivo. *Biochemistry,* 48, 817-819.
8) Sterner, R. and Liebl, W. (2001). Thermophilic adaptation of proteins. *Critical Reviews in Biochemistry and Molecular Biology* 36, 39-106.
9) Eijsink, V. G. H., Bjøork, A., Gåseidnes, S., Sirevåg, R., Synstad, B, van den Burg, B. and Vriend, G. (2004). Rational engineering of enzyme stability. *Journal of Biotechnology* 113, 105-120.
10) Wang, T. W., Zhu, H., Ma, X. Y., Ma, Y. S., Wei, D. Z. (2006). Structure-based stabilization of an enzyme: The case of penicillin acylase from *Alcaligenes faecalis*. *Protein and Peptide Letters* 13, 177-183.
11) Qi, X., Guo, Q., Wei, Y., Xu, H. Huang, R. (2012). Enhancement of pH stability and activity of glycerol dehydratase from *Klebsiella pneumoniae* by rational design. *Biotechnology Letters* 34, 339-346.
12) Brändén, C. and Tooze, J. In *Introduction to Protein Structure.* $2^{nd}$ Ed. ISBN 0-8153-2305-0. Garland publishing, NY.
13) Lin, C., Chao, Y., Xiangshan, Z., Yuanxing, Z. (2009). Rational introduction of disulfide bond to enhance optimal temperature of *Lipomyces starkeyi* alpha-dextranase expressed in *Pichia pastoris*. *Journal of Microbiology and Biotechnology* 19, 1506-1513
14) Pellequer, J.-L., Chen, S.-W., W. (2006). Multi-template approach to modeling engineered disulfide bonds. *Proteins—Structure Function and Bioinformatics* 65, 192-202.
15) Shortle, D. (1996). The denatured state (the other half of the folding equation) and its role in protein stability *FASEB J.* 10, 27-34.
16) Karlsson, M., Mårtensson, L.-G., Karlsson, C and Carlsson, U. (2005). Denaturant-assisted formation of a stabilizing disulfide bridge from engineered cysteines in nonideal conformations. *Biochemistry* 44, 3487-3493.
17) Mårtensson, L.-G., Karlsson, M. and Carlsson, U. (2002). Dramatic stabilization of the native state of human carbonic anhydrase II by an engineered disulfide bond. *Biochemistry* 41, 15867-15875.
18) Freskgård, P.-O., Carlsson, U., Mårtensson, L.-G., Jonsson, B.-H. (1991). Folding around the C-terminus of human carbonic anhydrase II—Kinetic characterization by use of a chemically reactive SH-group introduced by protein engineering. *FEBS letters* 289, 117-122.
19) Pace, C. N. and Shaw, K. L. (2000). Linear extrapolation method of analyzing solvent denaturation curves. *Proteins* 41, 1-7.
20) Wilbur, K. M. and Anderson, N. G. (1948). Electrometric and colorometric determination of carbonic anhydrase. *Journal of biological chemistry* 176, 147-154.

21) Rickli, E. E., Ghazanfar, S. A. S., Gibbons, B. H. and Edsall, J. T. (1964), Carbonic anhydrase from human erythrocytes. Preparation and properties of two enzymes. *Journal of biological chemistry*, 239, 1066-1078.
22) Khalifah R. G. (1971). The carbon dioxide hydration activity of carbonic anhydrase. Journal of biological chemistry 246, 2561-2573.
23) Armstrong J. M., Wyers, D. W., Verpoorte, J. A. and Edsall, J. T. (1966). Purification and properties of human erythrocyte carbonic anhydrases. *Journal of biological chemistry* 241, 5137-5149.
24) Cimini, S., Prisciandaro, M. and Barba, D. (2005). Simulation of a waste incineration process with flue-gas cleaning and heat recovery sections using Aspen plus. *Waste Management* 25, 171-175.
25) National Center for Biotechnology Information. URL: http://www.ncbi.nlm.nih.gov/

The invention claimed is:

1. An isolated polypeptide having carbonic anhydrase activity, the sequence of which corresponds to modified human carbonic anhydrase II, wherein the polypeptide comprises the mutations A23C, S99C, L202C, C205S and V241C relative to wild type human carbonic anhydrase II having the amino acid sequence of SEQ ID NO:9, has increased physical stability compared to wild type carbonic anhydrase II and further comprises disulfide bridges between C23 and C202 and/or between C99 and C241; and wherein the polypeptide comprises the amino acid sequence of SEQ ID NO: 8.

2. The isolated polypeptide having carbonic anhydrase activity according to claim 1, having a thermodynamic stability increased by 23.5 kJ/mol compared to wild type carbonic anhydrase II.

3. The isolated polypeptide having carbonic anhydrase activity according to claim 1, having a melting point increased by 18.5° C. compared to wild type carbonic anhydrase II.

4. The isolated polypeptide having carbonic anhydrase activity according to claim 1, having an activation energy of unfolding increased by 25 kJ/mol compared to wild type carbonic anhydrase II.

5. The isolated polypeptide having carbonic anhydrase activity according to claim 1, having a rate of unfolding in water at 21° C. that is about 22.000 times slower compared to wild type human carbonic anhydrase II.

6. The isolated polypeptide having carbonic anhydrase activity according to claim 1, having a half-life of 86 days at 60° C., 8 days at 65° C. and 1.6 days at 70° C.

7. The isolated polypeptide having carbonic anhydrase activity according to claim 1, wherein the isolated polypeptide maintains its increased physical stability compared to wild type carbonic anhydrase II in aqueous solutions of ethanol amines, comprising methyldiethanolamine (MDEA), monoethanolamine (MEA), diethanolamine (DEA), and aminoethoxyethanol.

8. A method of using an isolated polypeptide having carbonic anhydrase activity according to claim 1 for extraction of carbon dioxide from a carbon dioxide containing medium.

9. The method according to claim 8, wherein the isolated polypeptide having carbonic anhydrase activity is used in a bioreactor.

10. A method of preparing an isolated polypeptide of SEQ ID NO: 8, according to claim 1 comprising acceleration of the formation of disulfide bridges by incubation of the polypeptide at elevated temperatures of 25-60° C. in the presence of an oxidizing agent at a pH of 7-10.

* * * * *